(12) United States Patent
Stoilov et al.

(10) Patent No.: US 8,580,511 B2
(45) Date of Patent: Nov. 12, 2013

(54) TWO-COLOR FLUORESCENT REPORTER FOR ALTERNATIVE PRE-MRNA SPLICING

(75) Inventors: Peter G. Stoilov, Glendale, CA (US); Douglas L. Black, Santa Monica, CA (US)

(73) Assignee: The Regents of the University of California, Oakland, CA (US)

( * ) Notice: Subject to any disclaimer, the term of this patent is extended or adjusted under 35 U.S.C. 154(b) by 794 days.

(21) Appl. No.: 12/305,764

(22) PCT Filed: Jun. 19, 2007

(86) PCT No.: PCT/US2007/071582
§ 371 (c)(1),
(2), (4) Date: May 26, 2010

(87) PCT Pub. No.: WO2007/149870
PCT Pub. Date: Dec. 27, 2007

(65) Prior Publication Data
US 2010/0233685 A1    Sep. 16, 2010

Related U.S. Application Data

(60) Provisional application No. 60/814,965, filed on Jun. 19, 2006.

(51) Int. Cl.
*C07H 21/02* (2006.01)
*C07H 21/04* (2006.01)
*C12Q 1/68* (2006.01)
*C12N 15/00* (2006.01)

(52) U.S. Cl.
USPC ...... 435/6.13; 435/320.1; 536/23.1; 536/23.5

(58) Field of Classification Search
None
See application file for complete search history.

(56) References Cited

PUBLICATIONS

Kozak, M. (1986) Point mutations define a sequence flanking the AUG initiator codon that modulates translation by eukaryotic ribosomes. Cell 44: 283-292.*
Newman et al. (Apr. 2006) Identification of RNA-binding proteins that regulate FGFR2 splicing through the use of sensitive and specific dual color fluorescence minigene assays. RNA 12: 1129-1141.*
International Search Report mailed on Sep. 17, 2008, for International Application No. PCT/US2007/071582 filed on Jun. 19, 2007, 2 pages.
Levinson, N. et al., "Use of transcriptional synergy to augment sensitivity of a splicing reporter assay," *RNA*, 2006, vol. 12, No. 5, pp. 925-930.

* cited by examiner

*Primary Examiner* — Anne-Marie Falk
(74) *Attorney, Agent, or Firm* — Morgan, Lewis & Bockius LLP; Annette S. Parent

(57) ABSTRACT

The present invention provides reporter constructs for in vivo or in vitro monitoring of alternative pre-mRNA splicing events. The reporter constructs described herein are also particularly useful for high-throughput screening of compounds that affect alternative pre-mRNA splicing. Kits comprising the reporter constructs of the present invention find utility in a wide range of applications including, for example, basic research, drug screening, and drug design.

19 Claims, 13 Drawing Sheets

TWO-COLOR FLUORESCENT REPORTER FOR ALTERNATIVE PRE-MRNA SPLICING

CROSS REFERENCE TO RELATED APPLICATIONS

This application is a 371 of PCT/US07/71582 filed Jun. 19, 2007 which claims benefit of U.S. Provisional Application No. 60/814,965 filed on Jun. 19, 2006, all of which are incorporated herein by reference in their entireties.

STATEMENT OF GOVERNMENT RIGHTS

This invention was made with Government support under Grant No. R24GM70857 awarded by the National Institutes of Health and the National Institute of General Medical Sciences. The Government has certain rights in the invention.

BACKGROUND OF THE INVENTION

Currently available techniques for detecting alternative pre-mRNA splicing rely on the use of fluorescent or enzymatic reporter systems which produce a single reporter protein (see, e.g., Wagner et al., *Methods Mol. Biol.*, 257:29-46 (2004)). The single reporter construct is usually co-transfected with a reporter for a second protein as an expression control. Typically, an alternative cassette exon disrupts the translation of the reporter protein when included in the mature mRNA. The skipping of the alternative exon generates the functional mRNA and protein, while all other events (e.g., aberrant splicing, general inhibition of splicing, inhibition of transcription and translation) will abolish the expression of the reporter.

A major drawback of these reporter systems, however, is their inability to distinguish between general inhibition of splicing and selection of the particular alternative splicing events. In addition, the dynamic range of these reporter systems is relatively narrow. Such limitations make currently available reporter systems practical only for the detection of major changes in pre-mRNA splicing.

As such, there is a need in the art for reporter systems which are capable of detecting alternative pre-mRNA splicing with increased specificity, sensitivity, and versatility. The present invention satisfies this and other needs.

BRIEF SUMMARY OF THE INVENTION

The present invention provides reporter constructs for in vivo or in vitro monitoring of alternative pre-mRNA splicing events. The reporter constructs described herein are also particularly useful for high-throughput screening of compounds that affect alternative pre-mRNA splicing. Kits comprising the reporter constructs of the present invention find utility in a wide range of applications including, for example, basic research, drug screening, and drug design.

In one aspect, the present invention provides an alternative pre-mRNA splicing reporter construct comprising an expression control sequence (e.g., promoter) operably linked to a nucleic acid sequence encoding first and second reporter proteins, wherein the nucleic acid sequence encoding the first reporter protein comprises a first start codon that resides in a Kozak consensus sequence and that is interrupted by a cassette comprising a nucleic acid with alternative splice sites, wherein the alternative splice sites produce at least two alternative splice products, wherein the nucleic acid sequence encoding the second reporter protein comprises a second start codon that resides in a Kozak consensus sequence, wherein the nucleic acid sequence encoding the second reporter protein is 3' to the nucleic acid sequence encoding the first reporter protein, and wherein the first start codon is the only start codon in a Kozak consensus sequence that resides upstream of the second start codon.

In some embodiments, the first and second reporter proteins comprise independently selected fluorescent proteins. Examples of fluorescent proteins suitable for use in the present invention include, but are not limited to, green fluorescent protein, red fluorescent protein, yellow fluorescent protein, cyan fluorescent protein, blue fluorescent protein, and variants thereof. In other embodiments, the first and second reporter proteins comprise independently selected enzymatic proteins. Non-limiting examples of enzymatic proteins include luciferase, chloramphenicol acetyltransferase, β-galactosidase, β-glucuronidase, horseradish peroxidase, xylanase, alkaline phosphatase, and the like. In further embodiments, the first reporter protein comprises a fluorescent protein and the second reporter protein comprises an enzymatic protein, or vice versa.

In a preferred aspect, the present invention provides an alternative pre-mRNA splicing reporter construct comprising a promoter operably linked to a nucleic acid sequence encoding first and second fluorescent proteins, wherein the nucleic acid sequence encoding the first fluorescent protein comprises a first start codon that resides in a Kozak consensus sequence and that is interrupted by a cassette comprising a nucleic acid with alternative splice sites, wherein the alternative splice sites produce at least two alternative splice products, wherein the nucleic acid sequence encoding the second fluorescent protein comprises a second start codon that resides in a Kozak consensus sequence, wherein the nucleic acid sequence encoding the second fluorescent protein is 3' to the nucleic acid sequence encoding the first fluorescent protein, and wherein the first start codon is the only start codon in a Kozak consensus sequence that resides upstream of the second start codon.

In certain instances, the nucleic acid cassette with alternative splice sites comprises an exon flanked by two introns, an intron with two 5' splice sites and one 3' splice site, or an intron with one 5' splice site and two 3' splice sites. The alternative splice sites present in the nucleic acid cassette typically produce at least two, three, four, five, six, seven, eight, nine, ten, or more alternative splice products. In some embodiments, alternative (e.g., aberrant) splicing of an exon in the nucleic acid cassette is associated with a disease state. Preferably, the exon in the nucleic acid cassette comprises exon 10 of the human tau gene, the alternative splicing of which is associated with neurodegenerative disorders. In other embodiments, alternative (e.g., aberrant) splicing of an intron in the nucleic acid cassette is associated with a disease state. Additional disease states include, but are not limited to, tumorigenesis and cell transformation (e.g., various types of cancer), metabolic diseases and disorders, angiogenesis, muscular dystrophies, and inflammatory and autoimmune responses.

Non-limiting examples of promoters include a human cytomegalovirus (CMV) promoter, a long terminal repeat (LTR) or simian virus 40 (SV40) retroviral promoter, an *E. coli* lac or trp promoter, a phage lambda $P_L$ or $P_R$ promoter, a T3 or T7 promoter, a herpes simplex virus thymidine kinase (HSV-TK) promoter, a mouse metallothionein-I promoter, and the like. Preferably, the promoter comprises a CMV promoter. One skilled in the art will appreciate that other promoters known to control the expression of genes in prokaryotic or eukaryotic cells or their viruses are suitable for use in the present invention.

In some embodiments, the first fluorescent protein comprises a green fluorescent protein such as, for example, an enhanced green fluorescent protein (EGFP) or a variant thereof. A non-limiting example of an EGFP variant includes a destabilized version of EGFP. Preferably, the EGFP variant comprises a destabilized version of EGFP with modified internal ATG codons, e.g., the nucleic acid sequence set forth in SEQ ID NO:4 with a modified mouse ornithine decarboxylase (MODC) PEST sequence (SEQ ID NO:5) at the 3' end. In other embodiments, the second fluorescent protein comprises a red fluorescent protein such as, for example, a *Discosoma striata* red fluorescent protein (DsRed) or a variant thereof. A non-limiting example of a DsRed variant includes a destabilized version of DsRed-Express (SEQ ID NO:6).

In further embodiments, the present invention provides vectors (e.g., plasmids) and host cells comprising a reporter construct described herein, e.g., a two-color fluorescent alternative splicing reporter construct. Kits comprising one or more reporter constructs of the present invention are also provided, wherein the kits can optionally further comprise appropriate prokaryotic or eukaryotic host cells, directions for introducing the reporter constructs into cells, directions for detecting the expression of the first and second reporter (e.g., fluorescent and/or enzymatic) proteins. In some instances, the kits provide a vector comprising the reporter construct as a component of the vector. In other instances, the kits provide the reporter construct as a nucleic acid fragment suitable for cloning into an appropriate vector. In another embodiment, the kit comprises cells that express the reporter construct.

In another aspect, the present invention provides a method for monitoring alternative pre-mRNA splicing in a cell, the method comprising:
  (a) introducing a reporter construct described herein into the cell;
  (b) transcribing a pre-mRNA sequence from the reporter construct; and
  (c) detecting alternative splicing from the pre-mRNA sequence, wherein expression of the first reporter (e.g., fluorescent and/or enzymatic) protein indicates that a first alternative splice product has been produced, and wherein expression of the second reporter (e.g., fluorescent and/or enzymatic) protein indicates that a second alternative splice product has been produced.

In a preferred embodiment, the first and second reporter proteins each independently comprise a fluorescent protein. Non-limiting examples of fluorescent proteins include green fluorescent protein, red fluorescent protein, yellow fluorescent protein, cyan fluorescent protein, blue fluorescent protein, and variants thereof. In some embodiments, the first fluorescent protein comprises a green fluorescent protein such as, for example, an enhanced green fluorescent protein (EGFP) or a variant thereof (e.g., destabilized EGFP with modified internal ATG codons). In other embodiments, the second fluorescent protein comprises a red fluorescent protein such as, for example, a *Discosoma striata* red fluorescent protein (DsRed) or a variant thereof (e.g., destabilized DsRed-Express).

In some embodiments, the method can further comprise introducing a control reporter construct into a control cell to detect the presence or absence of a difference in ribosome scanning processivity between the first and the second alternative splice products. In other embodiments, two control reporter constructs are introduced into the control cell: (1) a first control reporter detecting the expression from a translation start codon in close proximity to the 5' end of the transcribed mRNA; (2) and a second control reporter detecting the expression from a translation start codon located further downstream from the 5' end of the transcribed mRNA. The control cell is typically a cell of the same or similar tissue type as the cell of interest (i.e., test cell). Non-limiting examples of control reporter constructs suitable for use in the present invention are illustrated in FIG. 2 and described in Example 1.

The method of the present invention can further comprise calculating a ratio of the expression levels of the first and second fluorescent proteins in the test cell (e.g., RFP/GFP ratio). In certain instances, the expression ratio in the test cell is compared to an expression ratio of the first and second fluorescent proteins in a control cell. Preferably, a change in the expression ratio in the test cell relative to the control cell indicates a modulation in alternative pre-mRNA splicing, e.g., a change in the level of the first alternative splice product compared to the level of the second alternative splice product.

In some embodiments, the modulation in alternative pre-mRNA splicing of the nucleic acid with alternative splice sites is associated with a disease state. In certain instances, alternative (e.g., aberrant) splicing of an exon (e.g., tau exon 10) in the nucleic acid cassette is associated with a disease state. In certain other instances, alternative (e.g., aberrant) splicing of an intron in the nucleic acid cassette is associated with a disease state. Examples of disease states include, but are not limited to, tumorigenesis and cell transformation (e.g., various types of cancer), neurodegenerative disorders, metabolic diseases and disorders, angiogenesis, muscular dystrophies, and inflammatory and autoimmune responses.

In yet another aspect, the present invention provides a method for identifying a compound that modulates alternative pre-mRNA splicing, the method comprising:
  (a) contacting a test cell expressing a reporter construct described herein with a compound; and
  (b) determining the effect of the compound on the expression of the first and second reporter (e.g., fluorescent and/or enzymatic) proteins, thereby identifying a compound that modulates alternative pre-mRNA splicing.

In a preferred embodiment, the first and second reporter proteins each independently comprise a fluorescent protein. Non-limiting examples of fluorescent proteins are described herein and include green fluorescent protein, red fluorescent protein, yellow fluorescent protein, cyan fluorescent protein, blue fluorescent protein, and variants thereof. In some embodiments, the first fluorescent protein comprises a green fluorescent protein such as, for example, an enhanced green fluorescent protein (EGFP) or a variant thereof (e.g., destabilized EGFP with modified internal ATG codons). In other embodiments, the second fluorescent protein comprises a red fluorescent protein such as, for example, a *Discosoma striata* red fluorescent protein (DsRed) or a variant thereof (e.g., destabilized DsRed-Express).

The screening method of the present invention can further comprise calculating a ratio of the expression levels of the first and second fluorescent proteins in the test cell (e.g., RFP/GFP ratio). In certain instances, the expression ratio in the test cell is compared to an expression ratio of the first and second fluorescent proteins in a control cell. The control cell is typically a cell of the same or similar tissue type as the test cell. Preferably, a change in the expression ratio in the test cell relative to the control cell indicates that the compound modulates alternative pre-mRNA splicing, e.g., the compound produces a change in the level of the first alternative splice product compared to the level of the second alternative splice product.

Other objects, features, and advantages of the present invention will be apparent to one of skill in the art from the following detailed description and figures.

DETAILED DESCRIPTION OF THE INVENTION

I. Introduction

Figure 1:
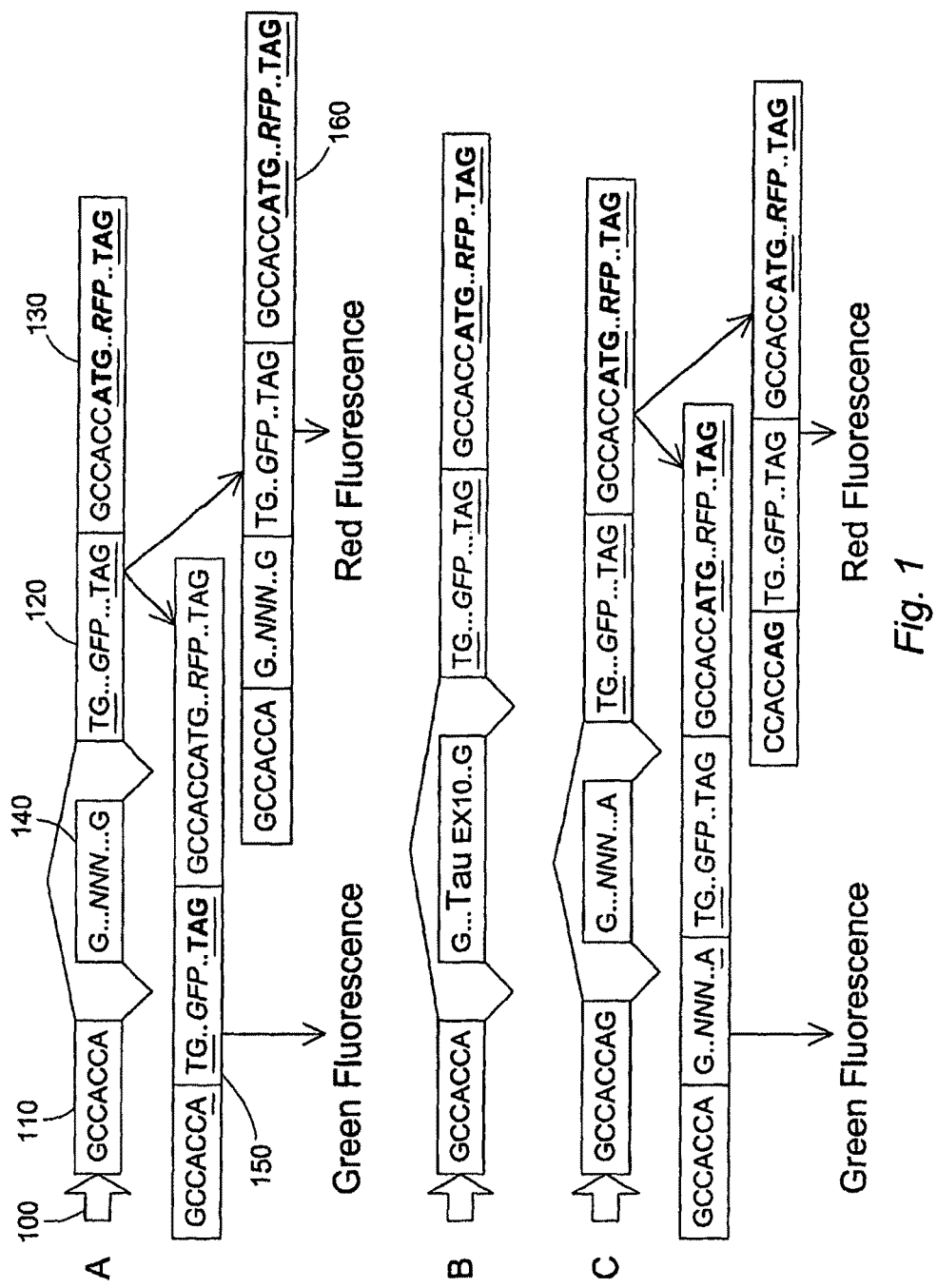
FIG. 1 shows several embodiments of the two-color fluorescent reporter constructs of the present invention.

The present invention provides reporter constructs which advantageously detect or monitor alternative pre-mRNA splicing with increased specificity, sensitivity, and versatility over currently available splicing reporter systems. In particular, the use of two fluorescent reporter molecules that are specific for the two alternative mRNAs generated by alternative splicing enables clear separation of alternative splicing events from other cellular processes such as transcription, translation, constitutive splicing, and the like. Additionally, the use of two fluorescent reporter molecules and the measurement of the ratio between their expression levels increases the dynamic range by multiplying the detection range of one reporter molecule by that of the other. Assuming similar detection ranges, this effectively squares the detection range compared to any single reporter system. Furthermore, constructs comprising two fluorescent reporter molecules are versatile because they are less affected by the size, sequence, and reading frame of the alternative exon or the presence or absence of ATG codons in the alternative exon. Thus, the reporter constructs described herein find utility in monitoring a wide range of cassette exons, alternative 3' and 5' splice sites, retained introns, and mutually exclusive exons.

Alternative splicing has been shown to play a role in a wide array of human diseases including, but not limited to, spinal muscular atrophy (SMA), spinal cerebellar ataxia (SCA), fragile X syndrome, frontotemporal dementia with Parkinsonism linked to chromosome 17 (FTPD-17), autism, severe combined immunodeficiency disease (SCID), familial dysautonomia, ataxia telangiectasia, neurofibromatosis type 1 (NF-1), myotonic dystrophy, and multiple types of cancer. As a result, the ability to modulate aberrant alternative splicing events may provide an effective treatment for some or all of these diseases. In addition, the modulation of alternative splicing in the muscle can be used for the treatment of muscular dystrophy by stimulating the expression of rare splice variants of dystrophin. Thus, the reporter constructs of the present invention can be used to identify a whole repertoire of drugs and other compounds that can be used to treat diseases or disorders associated with aberrant alternative pre-mRNA splicing.

II. Definitions

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice the present invention. For purposes of the present invention, the following terms are defined.

The term "nucleic acid" or "polynucleotide" includes a deoxyribonucleotide or ribonucleotide polymer in either single-stranded or double-stranded form, and, unless specifically indicated otherwise, encompasses polynucleotides containing known analogs of naturally-occurring nucleotides that can function in a similar manner as naturally-occurring nucleotides. It will be understood that when a nucleic acid molecule is represented by a DNA sequence, this also includes RNA molecules having the corresponding RNA sequence in which "U" (uridine) replaces "T" (thymidine).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (see, e.g., Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)).

The term "pre-mRNA," "precursor mRNA," or "primary RNA transcript" refers to a strand of messenger ribonucleic acid (mRNA), synthesized from a DNA template in the nucleus of a cell by transcription, prior to processing events such as splicing. Generally, eukaryotic pre-mRNA exists only briefly before it is fully processed into mature mRNA. Pre-mRNA includes two different types of segments, exons and introns. Most of exons encode protein, while introns are usually excised before translation by a process known as splicing. Spliceosomes, small organelles found in the nucleus and composed of protein and RNA, perform the excision. Additional processing steps attach modifications to the "front" (5') and "back" (3') ends of the mRNA. These non-coding segments include, for example, a 5' cap of 7-methylguanosine and a poly-A tail. When the mRNA has been properly processed, it is exported out of the nucleus and to ribosomes for translation.

A "splice site," in the context of a pre-mRNA molecule, refers to the short conserved sequence at the 5' end (donor site) or 3' end (acceptor site) of an intron to which a spliceosome binds and catalyzes the splicing of the intron from the pre-mRNA. An "alternative splice site" refers to additional donor and acceptor splice sites that can be used in to create alternative mRNAs from a single pre-mRNA. Alternative splice sites can reside in either intronic or exonic sequences. The use of alternative splice sites in pre-mRNA splicing may produce splice variants which differ in the length of an exon or in the presence or absence of an exon.

The term "splice variants" includes products of alternative splicing of a pre-mRNA molecule. After transcription, an initial nucleic acid transcript (i.e., pre-mRNA) may be spliced such that different (alternative) nucleic acid splice products (mRNAs) encode different polypeptides. Mechanisms for the production of splice variants vary, but include alternative splicing of exons. Alternate polypeptides derived from the same nucleic acid by read-through transcription are also encompassed by this definition. Any products of a splicing reaction, including recombinant forms of the splice products, are included in this definition.

The term "alternative splicing" or "alternative pre-mRNA splicing" as used herein refers to a process by which a gene can encode for multiple mRNA and protein products by differentially selecting which exons are to be included in a mature transcript. The process of alternative splicing can yield different mRNA molecules from a given gene by altering one or more of the following: (1) the transcription initiation site, thereby modifying the 5' end of the RNA; (2) the site of cleavage and polyadenylation, thereby altering the 3' end of the transcript; and (3) the retention of one or more introns or parts of introns and/or the exclusion of one or more exons or parts of exons, thereby altering the sequence of amino acids in the expressed protein. As such, in certain instances, alternative splicing involves the decision of whether or not to remove an intron, the alternative use of 5' splice sites, or the alternative use of 3' splice sites, wherein the length of an exon changes. In certain other instances, alternative splicing involves the decision of whether or not to include or skip an exon, wherein one or more alternatively used exons can optionally be included.

The term "Kozak consensus sequence" or "Kozak consensus" refers to the nucleotide sequence (GCC)GCC(A/G) CCAUGG (SEQ ID NO:1) on eukaryotic mRNA, wherein the (A/G) is a purine nucleotide three bases upstream of the start codon (AUG) and the (GCC) is a less conserved series of nucleotides. The Kozak consensus sequence on an mRNA molecule is generally recognized by a ribosome as the translational start site, from which point a protein is coded by that mRNA molecule. The ribosome may recognize the Kozak consensus sequence or a variation thereof to initiate translation and the amount of protein synthesized from a given mRNA molecule is usually dependent on the strength of the Kozak sequence. Some nucleotides in the sequence are more important than others. For example, the AUG series of nucleotides is essential since it is the actual start codon of the protein. For a "strong" consensus, the nucleotides at positions +4 (i.e., G in the consensus) and −3 (i.e., either A or G in the consensus) relative to the A nucleotide in the AUG start codon (i.e., position +1) should match the Kozak consensus sequence. An "adequate" consensus typically comprises one of these sites, while a "weak" consensus generally has neither. In certain instances, the C nucleotides at positions −5 and −2 relative to the A nucleotide in the AUG start codon (i.e., position +1) are not as conserved, but contribute to the overall strength of the Kozak consensus sequence.

A "cloning site" as used herein includes a segment of DNA which contains 1, 2, 3, 4, 5, 6, 7, 8, 9, 10, 11, 12, 13, 14, 15, 16, 17, 18, 19, 20, or more restriction sites. Cloning sites which contain 2 or more restriction sites are typically referred to as "multiple cloning sites" or "polylinkers." With respect to the present invention, a cassette comprising a nucleic acid with alternative splice sites (e.g., an exon flanked by two introns, an intron with two 5' splice sites and one 3' splice site, an intron with one 5' splice site and two 3' splice sites, etc.) can be inserted into a cloning site (e.g., an intronic sequence containing multiple restriction sites) which disrupts (e.g., interrupts, splits, etc.) the start (ATG) codon of the nucleic acid sequence encoding the first reporter protein.

Reference to a polynucleotide "encoding" a polypeptide means that, upon transcription of the polynucleotide and translation of the mRNA produced therefrom, a polypeptide is produced. The encoding polynucleotide is considered to include both the coding strand, whose nucleotide sequence is identical to an mRNA, as well as its complementary strand. It will be recognized that such an encoding polynucleotide is considered to include degenerate nucleotide sequences, which encode the same amino acid residues. Nucleotide sequences encoding a polypeptide can include polynucleotides containing introns as well as the encoding exons.

The term "expression control sequence" refers to a nucleotide sequence that regulates the transcription or translation of a polynucleotide or the localization of a polypeptide to which to which it is operatively linked. Expression control sequences are "operatively linked" or "operably linked" when the expression control sequence controls or regulates the transcription and, as appropriate, translation of the nucleotide sequence (i.e., a transcription or translation regulatory element, respectively), or localization of an encoded polypeptide to a specific compartment of a cell. Thus, an expression control sequence can be a promoter, enhancer, transcription terminator, a start codon (ATG), a splicing signal for intron excision and maintenance of the correct reading frame, a stop codon, a ribosome binding site, or a sequence that targets a polypeptide to a particular location, for example, a cell compartmentalization signal, which can target a polypeptide to the cytosol, nucleus, plasma membrane, endoplasmic reticulum, mitochondrial membrane or matrix, chloroplast membrane or lumen, medial trans-Golgi cisternae, or a lysosome or endosome. Cell compartmentalization domains are well known in the art and include, for example, a peptide containing amino acid residues 1 to 81 of human type II membrane-anchored protein galactosyltransferase, or amino acid residues 1 to 12 of the presequence of subunit IV of cytochrome c oxidase (see, also, Hancock et al., *EMBO J.,* 10:4033-4039 (1991); Buss et al., *Mol. Cell. Biol.,* 8:3960-3963 (1988); and U.S. Pat. No. 5,776,689).

"Inhibitors", "activators", and "modulators" refer to activating, inhibitory, or modulating molecules identified using assays described herein. Inhibitors are compounds that, e.g., bind to, partially or totally block activity, decrease, prevent, delay activation, inactivate, desensitize, or down regulate alternative splicing, e.g., antagonists. "Activators" are compounds that increase, open, activate, facilitate, enhance activation, sensitize, agonize, or up regulate alternative splicing, e.g., agonists. Inhibitors, activators, or modulators include antibodies, peptides, cyclic peptides, polypeptides, nucleic acids, cDNAs, antisense molecules, siRNA, ribozymes, small organic molecules and the like.

Samples or assays that are treated with a potential activator, inhibitor, or modulator are compared to control samples without the inhibitor, activator, or modulator to examine the extent of inhibition. Control samples (untreated with inhibitors) are assigned a relative protein activity value of 100%. Inhibition is achieved when the activity value relative to the control is about 80%, preferably 50%, more preferably 25-0%. Activation is achieved when the activity value relative to the control (untreated with activators) is 110%, more preferably 150%, more preferably 200-500% (i.e., two to five fold higher relative to the control), more preferably 1000-3000% higher.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid, fatty acid, polynucleotide, oligonucleotide, siRNA, cyclic peptide, etc., to be tested for the capacity to directly or indirectly modulation tumor cell proliferation. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

An "siRNA" molecule or an "RNAi molecule refers to a nucleic acid that forms a double stranded RNA, which double stranded RNA has the ability to reduce or inhibit expression of a gene or target gene when the siRNA expressed in the same cell as the gene or target gene. "siRNA" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is 15-50 nucleotides in length, and the double stranded siRNA is about 15-50 base pairs in length, preferable about preferably about 20-30 base nucleotides, preferably about 20-25 or about 24-29 nucleotides in length, e.g., 20, 21, 22, 23, 24, 25, 26, 27, 28, 29, or 30 nucleotides in length. See also PCT/US03/07237, herein incorporated by reference in its entirety.

An siRNA molecule or RNAi molecule is "specific" for a target nucleic acid if it reduces expression of the nucleic acid by at least about 10% when the siRNA or RNAi is expressed in a cell that expresses the target nucleic acid.

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally-occurring amino acid, as well as to naturally-occurring amino acid polymers and non-naturally occurring amino acid polymers.

The term "amino acid" refers to naturally-occurring and synthetic amino acids, as well as amino acid analogs and amino acid mimetics that function in a manner similar to the naturally-occurring amino acids. Naturally-occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally-occurring amino acid, i.e., an α carbon that is bound to a hydrogen, a carboxyl group, an amino group, and an R group, e.g., homoserine, norleucine, methionine sulfoxide, and methionine methyl sulfonium. Such analogs have modified R groups (e.g., norleucine) or modified peptide backbones, but retain the same basic chemical structure as a naturally-occurring amino acid. Amino acid mimetics refers to chemical compounds that have a structure that is different from the general chemical structure of an amino acid, but that functions in a manner similar to a naturally-occurring amino acid.

Amino acids may be referred to herein by either their commonly known three-letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill in the art will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill in the art will recognize that individual substitutions, deletions, or additions to a nucleic acid, peptide, polypeptide, or protein sequence which alters, adds, or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the present invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

The term "isolated" or "purified" refers to a material that is substantially or essentially free from components that normally accompany the material in its native state in nature. Purity or homogeneity generally are determined using analytical chemistry techniques such as polyacrylamide gel electrophoresis, high performance liquid chromatography, and the like. A polynucleotide or a polypeptide is considered to be isolated when it is the predominant species present in a preparation. Generally, an isolated protein or nucleic acid molecule represents greater than 80% of the macromolecular species present in a preparation, often represents greater than 90% of all macromolecular species present, usually represents greater than 95% of the macromolecular species, and, in particular, is a polypeptide or polynucleotide that is purified to essential homogeneity such that it is the only species detected when examined using conventional methods for determining purity of such a molecule.

The term "identical" or "percent identity," in the context of two or more nucleic acid or polypeptide sequences, refers to two or more sequences or subsequences that are the same or have a specified percentage of amino acid residues or nucleotides that are the same (e.g., about 60% identity, preferably about 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithm with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the complement of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is about 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from about 20 to about 600, usually from about 50 to about 200, more usually from about 100 to about 150, in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman, *Adv. Appl. Math.*, 2:482 (1981), by the homology alignment algorithm of Needleman and Wunsch, *J. Mol. Biol.*, 48:443 (1970), by the search for similarity method of Pearson and Lipman, *Proc. Natl. Acad. Sci. USA*, 85:2444 (1988), by computerized implementations of these algorithms (e.g., GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1987-2005, Wiley Interscience)).

A preferred example of algorithms suitable for determining percent sequence identity and sequence similarity are the BLAST and BLAST 2.0 algorithms, which are described in Altschul et al., *Nuc. Acids Res.*, 25:3389-3402 (1977) and Altschul et al., *J. Mol. Biol.*, 215:403-410 (1990), respectively. BLAST and BLAST 2.0 are used, with the parameters described herein, to determine percent sequence identity for the nucleic acids and proteins of the present invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value;

the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length of 3, and expectation (E) of 10, and the BLOSUM62 scoring matrix (see, e.g., Henikoff et al., Proc. Natl. Acad. Sci. USA, 89:10915 (1989)) alignments (B) of 50, expectation (E) of 10, M=5, N=−4, and a comparison of both strands.

As used herein, the term "vector" is used in reference to nucleic acid molecules that transfer DNA segment(s) from one cell to another. The term "expression vector" refers to a recombinant DNA molecule containing one or more desired coding sequences and appropriate nucleic acid sequences necessary for the expression of the operably linked coding sequence(s) in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The term "cell" or "host cell" is intended to include any eukaryotic or prokaryotic cell (e.g., bacterial cells such as E. coli, yeast cells, mammalian cells, avian cells, amphibian cells, plant cells, fish cells, insect cells, etc.), whether located in vitro (e.g., in cell culture) or in vivo (e.g., in a living organism).

The term "transfection" as used herein refers to the introduction of foreign DNA into eukaryotic cells. Transfection may be accomplished by a variety of means known in the art including, but not limited to, calcium phosphate-DNA co-precipitation, DEAE-dextran-mediated transfection, polybrene-mediated transfection, electroporation, microinjection, liposome fusion, lipofection, protoplast fusion, retroviral infection, and biolistics. "Stable transfection" or "stably transfected" refers to the introduction and integration of foreign DNA into the genome of the transfected cell. "Transient transfection" or "transiently transfected" refers to the introduction of foreign DNA into a cell where the foreign DNA fails to integrate into the genome of the transfected cell, but instead persists in the nucleus of the transfected cell for several days. During this time, the foreign DNA is subject to the regulatory controls that govern the expression of endogenous genes.

The term "reporter" is intended to include any of a variety of proteins that produce a signal which can be detected (i.e., visualized) using techniques known in the art, as well as nucleic acids encoding such proteins. Examples of reporters include, but are not limited to, fluorescent reporters such as green fluorescent protein, red fluorescent protein, yellow fluorescent protein, cyan fluorescent protein, blue fluorescent protein, and variants thereof; and enzymatic reporters such as luciferase, chloramphenicol acetyltransferase, β-galactosidase, β-glucuronidase, horseradish peroxidase, alkaline phosphatase, and the like.

As used herein, the term "fluorescent protein" refers to any protein that can fluoresce when excited with an appropriate electromagnetic radiation. In general, a fluorescent protein useful in the context of the present invention derives its fluorescence from autocatalytically forming a chromophore. A fluorescent protein can contain amino acid sequences that are naturally-occurring or that have been engineered (e.g., variants or mutants). When used in reference to a fluorescent protein, the term "mutant" or "variant" refers to a protein that is different from a reference protein. For example, a spectral variant of Aequorea victoria green fluorescent protein (GFP) can be derived from the naturally-occurring GFP by engineering mutations such as amino acid substitutions into the reference GFP protein as described in, e.g., U.S. Pat. Nos. 6,403,374 and 6,800,733. Similarly, a monomeric or dimeric variant of Discosoma striata red fluorescent protein (DsRed) can be derived from the naturally-occurring DsRed by engineering mutations such as amino acid substitutions into the DsRed protein as described in, e.g., U.S. Pat. No. 7,157,566.

The term "green fluorescent protein" or "GFP" is used broadly herein to refer to a protein that fluoresces green light, for example, Aequorea victoria GFP. GFPs have been isolated from the Pacific Northwest jellyfish, Aequorea victoria, the sea pansy, Renilla reniformis, and Phialidium gregarium (Ward et al., Photochem. Photobiol., 35:803-808 (1982); Levine et al., Comp. Biochem. Physiol., 72B:77-85 (1982)). Similarly, reference is made herein to GFP variants such as, e.g., "yellow fluorescent protein" or "YFP," which fluoresces yellow, "cyan fluorescent protein" or "CFP," which fluoresces cyan, "blue fluorescent protein" or "BFP," which fluoresces blue, and the like. Specific examples of GFP variants include, but are not limited to, enhanced GFP (EGFP), destabilized EGFP, the modified EGFP sequence set forth in SEQ ID NO:4, the modified EYFP sequence set forth in SEQ ID NO:7, the GFP variants described in Doan et al., Mol. Microbiol., 55:1767-1781 (2005), the GFP variant described in Crameri et al., Nat. Biotechnol., 14:315-319 (1996), the cerulean fluorescent proteins described in Rizzo et al., Nat. Biotechnol., 22:445 (2004) and Tsien, Annu. Rev. Biochem., 67:509 (1998), and the yellow fluorescent protein described in Nagal et al., Nat. Biotechnol., 20:87-90 (2002).

The term "red fluorescent protein" or "RFP" is used in the broadest sense and specifically covers DsRed, the RFP isolated from the corallimorph Discosoma striata (Matz et al., Nature Biotech., 17:969-973 (1999)), and red fluorescent proteins from any other species, such as coral and sea anemone, as well as variants thereof as long as they retain the ability to fluoresce red light. Other DsRed variants are described in, e.g., Shaner et al., Nat. Biotechnol., 22:1567-1572 (2004), and include mStrawberry (GenBank Acc. No. AY678266), mCherry (GenBank Acc. No. AY678264), mOrange (GenBank Acc. No. AY678265), mBanana (GenBank Acc. No. AY678267), mHoneydew (GenBank Acc. No. AY678271), and mTangerine (GenBank Acc. No. AY678270). Additional DsRed variants are described in, e.g., Wang et al., Proc. Natl. Acad. Sci. U.S.A., 101:16745-16749 (2004) and include mRaspberry (GenBank Acc. No. AY786536) and mPlum (GenBank Acc. No. AY786537). Further examples of DsRed variants include mRFPmars (GenBank Acc. No. CS569024) described in Fischer et al., FEBS Lett., 577:227-232 (2004) and mRFPruby described in Fischer et al., FEBS Lett., 580: 2495-2502 (2006).

III. Description of the Embodiments

The present invention provides, inter alia, reporter constructs for monitoring alternative pre-mRNA splicing events in living individual cells, cellular extracts, homogeneous or heterogeneous cell populations, and/or whole organisms. The reporter constructs described herein are also particularly useful for high-throughput screening of compounds that affect alternative pre-mRNA splicing. Kits comprising the reporter constructs of the present invention find utility in a wide range of applications including, for example, basic research, drug screening, and drug design. In certain preferred embodiments, the reporter constructs of the present invention detect or monitor alternative pre-mRNA splicing using a two-color fluorescent protein reporter system.

A. Fluorescent Proteins

Fluorescent proteins are widely used as reporters for the detection of cellular processes in living systems using optical microscopy and related methodology. A broad range of fluorescent protein genetic variants have been developed that feature fluorescence emission spectral profiles spanning almost the entire visible light spectrum (see, Table 1).

Mutagenesis efforts in the original *Aequorea victoria* jellyfish green fluorescent protein have resulted in new fluorescent probes that range in color from blue to yellow, and are some of the most widely used in vivo reporter molecules in biological research. Longer wavelength fluorescent proteins, emitting in the orange and red spectral regions, have been developed from the marine anemone, *Discosoma striata*, and reef corals belonging to the class Anthozoa. Still other species have been mined to produce similar proteins having cyan, green, yellow, orange, and deep red fluorescence emission.

TABLE 1

| Protein | Excitation Maximum (nm) | Emission Maximum (nm) | Molar Extinction Coefficient | Quantum Yield | In vivo Structure | Relative Brightness (% of EGFP) |
|---|---|---|---|---|---|---|
| GFP (wt) | 395/475 | 509 | 21,000 | 0.77 | Monomer* | 48 |
| Green Fluorescent Proteins | | | | | | |
| EGFP | 484 | 507 | 56,000 | 0.60 | Monomer* | 100 |
| AcGFP | 480 | 505 | 50,000 | 0.55 | Monomer* | 82 |
| TurboGFP | 482 | 502 | 70,000 | 0.53 | Monomer* | 110 |
| Emerald | 487 | 509 | 57,500 | 0.68 | Monomer* | 116 |
| Azami Green | 492 | 505 | 55,000 | 0.74 | Monomer | 121 |
| ZsGreen | 493 | 505 | 43,000 | 0.91 | Tetramer | 117 |
| Orange and Red Fluorescent Proteins | | | | | | |
| Kusabira Orange | 548 | 559 | 51,600 | 0.60 | Monomer | 92 |
| mOrange | 548 | 562 | 71,000 | 0.69 | Monomer | 146 |
| dTomato | 554 | 581 | 69,000 | 0.69 | Dimer | 142 |
| dTomato-Tandem | 554 | 581 | 138,000 | 0.69 | Monomer | 283 |
| DsRed | 558 | 583 | 75,000 | 0.79 | Tetramer | 176 |
| DsRed2 | 563 | 582 | 43,800 | 0.55 | Tetramer | 72 |
| DsRed-Express (T1) | 555 | 584 | 38,000 | 0.51 | Tetramer | 58 |
| DsRed-Monomer | 556 | 586 | 35,000 | 0.10 | Monomer | 10 |
| mTangerine | 568 | 585 | 38,000 | 0.30 | Monomer | 34 |
| mStrawberry | 574 | 596 | 90,000 | 0.29 | Monomer | 78 |
| AsRed2 | 576 | 592 | 56,200 | 0.05 | Tetramer | 8 |
| mRFP1 | 584 | 607 | 50,000 | 0.25 | Monomer | 37 |
| JRed | 584 | 610 | 44,000 | 0.20 | Dimer | 26 |
| mCherry | 587 | 610 | 72,000 | 0.22 | Monomer | 47 |
| HcRed1 | 588 | 618 | 20,000 | 0.015 | Dimer | 1 |
| mRaspberry | 598 | 625 | 86,000 | 0.15 | Monomer | 38 |
| HcRed-Tandem | 590 | 637 | 160,000 | 0.04 | Monomer | 19 |
| mPlum | 590 | 649 | 41,000 | 0.10 | Monomer | 12 |
| AQ143 | 595 | 655 | 90,000 | 0.04 | Tetramer | 11 |
| Yellow Fluorescent Proteins | | | | | | |
| EYFP | 514 | 527 | 83,400 | 0.61 | Monomer* | 151 |
| Topaz | 514 | 527 | 94,500 | 0.60 | Monomer* | 169 |
| Venus | 515 | 528 | 92,200 | 0.57 | Monomer* | 156 |
| mCitrine | 516 | 529 | 77,000 | 0.76 | Monomer | 174 |
| YPet | 517 | 530 | 104,000 | 0.77 | Monomer* | 238 |
| PhiYFP | 525 | 537 | 124,000 | 0.39 | Monomer* | 144 |
| ZsYellow1 | 529 | 539 | 20,200 | 0.42 | Tetramer | 25 |
| mBanana | 540 | 553 | 6,000 | 0.7 | Monomer | 13 |
| Blue Fluorescent Proteins | | | | | | |
| EBFP | 383 | 445 | 29,000 | 0.31 | Monomer* | 27 |
| Sapphire | 399 | 511 | 29,000 | 0.64 | Monomer* | 55 |
| T-Sapphire | 399 | 511 | 44,000 | 0.60 | Monomer* | 79 |
| Cyan Fluorescent Proteins | | | | | | |
| ECFP | 439 | 476 | 32,500 | 0.40 | Monomer* | 39 |
| mCFP | 433 | 475 | 32,500 | 0.40 | Monomer | 39 |
| Cerulean | 433 | 475 | 43,000 | 0.62 | Monomer* | 79 |
| CyPet | 435 | 477 | 35,000 | 0.51 | Monomer* | 53 |
| AmCyan1 | 458 | 489 | 44,000 | 0.24 | Tetramer | 31 |
| Midori-Ishi Cyan | 472 | 495 | 27,300 | 0.90 | Dimer | 73 |
| mTFP1 (Teal) | 462 | 492 | 64,000 | 0.85 | Monomer | 162 |

*Weak Dimer

Although native green fluorescent protein (GFP) produces significant fluorescence and is extremely stable, the excitation maximum is close to the ultraviolet range. Because ultraviolet light requires special optical considerations and can damage living cells, it is generally not well suited for live cell imaging with optical microscopy. Fortunately, the excitation maximum of GFP is readily shifted to 488 nm (in the cyan region) by introducing a single point mutation altering the serine at position 65 into a threonine residue (S65T). This mutation is featured in a variant of GFP known as enhanced GFP (EGFP), which is commercially available in a wide range of vectors offered by Clontech Laboratories, Inc. (Mountain View, Calif.). EGFP can be conveniently imaged using commonly available filter sets designed for fluorescein and is among the brightest of the currently available fluorescent proteins.

A variety of other GFP-related fluorescent proteins having useful excitation and emission spectra have been engineered by modifying the amino acid sequence of the naturally-occurring GFP from *Aequorea victoria* (see, e.g., Prasher et al., *Gene*, 111:229-233 (1992); Heim et al., *Proc. Natl. Acad. Sci. USA*, 91:12501-12504 (1994); U.S. Pat. No. 5,625,048; and PCT Publication No. WO96/23810). Additional GFP-related fluorescent proteins include, but are not limited to, allelic variants of native *Aequorea victoria* GFP (e.g., a variant having a Q80R substitution as described in Chalfie et al., *Science*, 263:802-805 (1994) and spectral variants of GFP (e.g., YFP, CFP, BFP, and enhanced or otherwise modified forms thereof as described in U.S. Pat. Nos. 6,150,176; 6,124,128; 6,077,707; 6,066,476; 5,998,204; and 5,777,079). GFP-related fluorescent proteins further include proteins having one or more folding mutations, and fragments of the proteins that are fluorescent, for example, an *Aequorea victoria* GFP from which the two N-terminal amino acid residues have been removed. Several of these fluorescent proteins contain different aromatic amino acids within the central chromophore and fluoresce at a distinctly shorter wavelength than the native GFP species.

With regard to red fluorescent proteins, the first coral fluorescent protein to be extensively utilized was derived from *Discosoma striata* and is commonly referred to as DsRed. Once fully matured, the fluorescence emission spectrum of DsRed features a peak at 583 nm, while the excitation spectrum has a major peak at 558 nm and a minor peak at about 500 nm. A second-generation DsRed, known as DsRed2, contains several mutations at the peptide N-terminus that prevent formation of protein aggregates and reduce toxicity. In addition, the fluorophore maturation time is reduced with these modifications. Further reductions in maturation time have been realized with the third generation of DsRed mutants, known as DsRed-Express, which also display an increased brightness level in terms of peak cellular fluorescence. Red fluorescence emission from DsRed-Express can be observed within an hour after expression, as compared to approximately six hours for DsRed2 and 11 hours for DsRed. A yeast-optimized variant, termed RedStar, has been developed that also has an improved maturation rate and increased brightness.

Other red fluorescent proteins have been isolated from various reef coral organisms. One of the first to be adapted for mammalian applications is HcRed1, which was isolated from *Heteractis crispa* and is commercially available from Clontech Laboratories, Inc. (Mountain View, Calif.). HcRed1 was originally derived from a non-fluorescent chromoprotein that absorbs red light through mutagenesis to produce a weakly fluorescent obligate dimer having an absorption maximum at 588 nm and an emission maximum of 618 nm. Additional red fluorescent proteins have been engineered by modifying the amino acid sequence of DsRed. For example, U.S. Patent Publication No. 20070099175 describes nucleic acid sequences encoding red fluorescent protein variants which contain at least one mutation corresponding to positions D59, I60, S62, P63, Q64, F65, Q66, S69, K70, V71, Y72, V73, W93, R95, N98, W143, A145, S146, T147, E148, Y151, G159, I161, K163, G171, S179, Y181, S197, L199, Y214, E215 or R216 of the DsRed amino acid sequence. These DsRed variants are associated with improved spectral and biochemical properties including improved folding, brightness, and sharpness, as well as more defined excitation and emission peaks, when expressed in mammalian cells.

The family of yellow fluorescent proteins was initiated after the crystal structure of green fluorescent protein revealed that threonine residue 203 (Thr203) was near the chromophore. Mutation of this residue to tyrosine was introduced to stabilize the excited state dipole moment of the chromophore and resulted in a 20 nm shift to longer wavelengths for both the excitation and emission spectra. Further refinements led to the development of the enhanced yellow fluorescent protein (EYFP), which is commercially available from Clontech Laboratories, Inc. (Mountain View, Calif.). The brightness and fluorescence emission spectrum of EYFP combine to make this probe an excellent candidate for multicolor imaging experiments in fluorescence microscopy. Continued development of fluorescent protein architecture for yellow emission has led to the Citrine variant of YFP, which is very bright relative to EYFP and has been demonstrated to be much more resistant to photobleaching, acidic pH, and other environmental effects. Another derivative, named Venus, is the fastest maturing and one of the brightest yellow variants developed to date. The coral reef protein, ZsYellow1, originally cloned from a *Zoanthus* species native to the Indian and Pacific oceans, produces true yellow emission and is ideal for multicolor applications.

The blue and cyan variants of green fluorescent protein resulted from direct modification of the tyrosine residue at position 66 (Y66) in the native fluorophore. Conversion of this amino acid to histidine results in blue emission having a wavelength maxima at 450 nm, whereas conversion to tryptamine results in a major fluorescence peak at about 480 nm along with a shoulder that peaks at about 500 nm. Both probes are only weakly fluorescent and require secondary mutations to increase folding efficiency and overall brightness. Even with modifications, the enhanced versions in this class of fluorescent protein (EBFP and ECFP) are about 25 to 40 percent as bright as EGFP. However, ECFP, which can be excited off-peak by an argon-ion laser (using the 457 nm spectral line), is significantly more resistant to photobleaching than the blue derivative.

Examples of improved cyan fluorescent proteins include AmCyan1 and an enhanced cyan variant known as Cerulean. Derived from the reef coral, *Anemonia majano*, the AmCyan1 fluorescent protein variant has been optimized with human codons to generate a high relative brightness level and resistance to photobleaching when compared to ECFP during mammalian expression. The Cerulean fluorescent protein was developed by site-directed mutagenesis of ECFP to yield a higher extinction coefficient and improved quantum yield.

In contrast to standard fluorescent proteins, which are extremely stable, destabilized fluorescent protein variants display rapid turnover rates. This shorter half-life makes destabilized variants ideal for use in quantitative reporter assays and kinetic studies. They can be used to accurately measure the kinetics of transient mRNA transcription from regulated promoters, monitor gene expression during development, or characterize cis-regulatory elements. Destabilized variants are also suitable for developing stably transformed cell lines because destabilized proteins can be expressed without excess buildup of protein.

The destabilized fluorescent protein variants are constructed by fusing a portion of mouse ornithine decarboxylase (MODC) to the C-terminus of the fluorescent protein. This region contains a PEST domain that targets the protein for degradation, giving the protein a substantially shorter half-life (Li et al., *J. Biol. Chem.*, 273:34970-34975 (1998)). In certain instances, point mutations in the MODC sequence can provide a fluorescent protein such as EGFP with an half-life of 50 minutes compared to 26 hours for the unmodified fluorescent protein (Corish et al., *Protein Eng.*, 12:1035-1040 (1999)). Destabilized variants can be used in cells from any organism that employ PEST sequence-mediated degradation pathways. As with other fluorescent proteins, destabilized fluorescent protein variants can be human codon-optimized and retain the same spectral properties as standard fluorescent proteins. Vectors encoding destabilized variants of fluorescent proteins such as EGFP and DsRed are commercially available, e.g., from Clontech Laboratories, Inc. (Mountain View, Calif.).

In general, the amount of fluorescence in a sample such as a cell or cellular extract can be measured using a fluorimeter, wherein excitation radiation from an excitation source having a first wavelength passes through excitation optics and causes the excitation radiation to excite the sample. In response, a fluorescent protein present in the sample emits radiation having a wavelength that is different from the excitation wavelength. Collection optics then collect the emission from the sample. The device can include a temperature controller to maintain the sample at a specific temperature while it is being scanned, and can have a multi-axis translation stage, which moves a microtiter plate holding a plurality of samples in order to position different wells to be exposed. The multi-axis translation stage, temperature controller, auto-focusing feature, and electronics associated with imaging and data collection can be managed by an appropriately programmed digital computer, which can also transform the data collected during the assay into another format for presentation. This process can be miniaturized and automated to enable screening many thousands of compounds in a high-throughput format. These and other methods of performing assays on fluorescent materials are well known in the art (see, e.g., Lakowicz, "Principles of Fluorescence Spectroscopy," Plenum Press (1983); Herman, "Resonance energy transfer microscopy," In "Fluorescence Microscopy of Living Cells in Culture," Part B, *Meth. Cell Biol.*, 30:219-243, Ed. Taylor and Wang, Academic Press (1989); and Turro, "Modern Molecular Photochemistry," Benjamin/Cummings Publ. Co., Inc., pp. 296-361 (1978)).

B. Two-Color Fluorescent Reporter Constructs

The translation of eukaryotic mRNA typically starts from the first AUG codon that is in the context of a Kozak consensus sequence. Although it can occur, the translation from AUG codons that do not reside in a Kozak consensus sequence is usually very inefficient. Another property of the eukaryotic translational machinery is its inability to translate a downstream open reading frame (ORF) in a polycistronic transcript. Exceptions include ORFs that use internal ribosome entry sites to initiate translation. These ORFs do not need a Kozak consensus sequence for efficient translation and can be translated when they are located downstream of other ORFs in polycistronic transcripts.

The two-color fluorescent reporter constructs for detecting alternative pre-mRNA splicing take advantage of the requirement of the eukaryotic translational apparatus for Kozak consensus sequences and its inability to translate downstream ORFs in polycistronic transcripts to ensure that a different reporter protein is expressed for each alternative splicing event. The reporter constructs typically contain two ORFs which encode two different fluorescent reporter proteins in a bicistronic transcript. A critical feature of the reporter constructs resides in the elimination or minimization of the use of AUG codons preceding the AUG codon of the second reporter protein when the AUG codon of the first reporter is disrupted because use of AUG codons upstream of the second reporter can significantly decrease or even abolish its expression.

In certain aspects, the AUG codon of the first ORF is split (i.e., interrupted) by an intronic sequence (e.g., the reporter intron set forth in SEQ ID NO:2, an intron from the human beta-globin gene, etc.) into which a cassette comprising a nucleic acid with alternative splice sites is inserted. Expression of the first reporter protein indicates that a first alternative splice product has been produced, wherein the AUG codon of the first ORF has been regenerated in the mature mRNA transcript by splicing. For example, expression of the first reporter protein from a reporter construct containing a cassette comprising an exon flanked by two introns indicates that the cassette has been spliced out of the pre-mRNA sequence. However, expression of the second reporter protein indicates that a second alternative splice product has been produced, wherein the AUG codon of the first ORF is disrupted, thereby preventing expression of the upstream first reporter protein and causing translation to initiate at the downstream AUG of the second reporter protein. For example, expression of the second reporter protein from a reporter construct containing a cassette comprising an exon flanked by two introns indicates that the exon from the cassette is spliced into the first ORF by means of alternative splicing.

The reporter constructs are typically engineered so that the first AUG with a Kozak consensus sequence downstream of the first reporter protein is the start codon for the second reporter protein. Thus, inclusion of the alternative exon both blocks the expression of the upstream first reporter protein and induces downstream expression of the second reporter protein. The ratio between the alternatively spliced isoforms can be assessed by measuring the expression of the two reporter proteins. In certain instances, changes in alternative splicing result in changes in the ratio of the two reporter proteins. In certain other instances, the coordinated increase or decrease of the expression of both reporter proteins, which does not change the expression ratio, will be indicative of general changes in splicing efficiency, splicing accuracy, transcription, and/or translation, but not of alternative splicing.

As a non-limiting example, the reporter constructs of the present invention can comprise two tandemly arranged open reading frames (ORFs), one for green fluorescent protein (GFP) and one for red fluorescent protein (RFP). A cassette comprising an alternatively spliced exon flanked by two introns splits the GFP translation start codon. When the alternative exon is skipped, the two parts of the GFP start codon are joined together and the GFP protein is translated from the resulting mRNA. The downstream RFP ORF is not translated because of the low efficiency with which eukaryotic ribosomes translate polycistronic mRNAs. If included, the alternative exon splits the GFP start codon and the downstream RFP translation start codon is used. In this case, the GFP coding region becomes the 5'-UTR for RFP. A number of the ATG codons upstream of the RFP start codon are mutated, while two ATG codons required for function in GFP are left intact but their Kozak sequences destroyed. These modifications to the internal ATG codons of GFP ensure that the GFP start codon is the only start codon upstream of the RFP start codon. Other mutations can also be made in the two proteins to further improve function.

The reporter constructs of the present invention are generally useful for detecting or monitoring the alternative splicing of exons in a gene of interest. Preferably, the exon from the gene of interest, together with at least 5, 10, 15, 20, 25, 30, 35, 40, 45, 50, 55, 60, 65, 70, 75, 80, 85, 90, 95, 100, or up to all of the nucleotides from each of the flanking intronic sequences, are inserted into the reporter construct as described above, introduced into cells, and monitored for the presence or level of alternative splicing events. Genes of interest include, but are not limited to, genes associated with disease states such as tumorigenesis and cell transformation, neurodegenerative disorders, metabolic diseases and disorders, angiogenesis, inflammatory and autoimmune responses, and the like.

Examples of gene sequences associated with tumorigenesis and cell transformation (e.g., cancer) include, but are not limited to, EGFR/HER1/ErbB1, HER2/Neu/ErbB2, HER3/ErbB3, HER4/ErbB4, VEGFR-1/FLT-1, VEGFR-2/FLK-1/KDR, VEGFR-3/FLT-4, FLT-3/FLK-2, PDGFRA, PDGFRB, c-KIT/SCFR, INSR (insulin receptor), IGF-IR, IGF-IIR, IRR (insulin receptor-related receptor), CSF-1R, FGFR-1, FGFR-2, FGFR-3, FGFR-4, HGFR-1, HGFR-2, CCK4, TRK-A, TRK-B, TRK-C, MET, RON, EPHA-1, EPHA-2, EPHA-3, EPHA-4, EPHA-5, EPHA-6, EPHA-7, EPHA-8, EPHB-1, EPHB-2, EPHB-3, EPHB-4, EPHB-5, EPHB-6, AXL, MER, TYRO3, TIE-1, TIE-2, TEK, RYK, DDR-1, DDR-2, RET, c-ROS, LTK (leukocyte tyrosine kinase), ALK (anaplastic lymphoma kinase), ROR-1, ROR-2, MUSK, AATYK-1, AATYK-2, AATYK-3, RTK 106, BCR-ABL, Src, Frk, Btk, Csk, Abl, Zap70, Fes/Fps, Fak, Jak, Ack, LIMK, Akt, MAPK/ERK, MEK, RAF, PLA2, MEKK, JNKK, JNK, p38, Shc (p66), PI3K, K-Ras, N-Ras, H-Ras, Rho, Rac1, Cdc42, PLC, PKC, p70 S6 kinase, p53, cyclin D1, STAT1, STAT3, PIP2, PIP3, PDK, mTOR, BAD, p21, p27, ROCK, IP3, TSP-1, NOS, PTEN, RSK-1, RSK-2, RSK-3, JNK, c-Jun, Rb, CREB, Ki67, and paxillin. As a non-limiting example, the alternative splicing of exon IIIb of FGFR-2, which is associated with well-differentiated prostate tumor cells, can be monitored using the reporter constructs of the present invention.

Non-limiting examples of gene sequences associated with neurodegenerative disorders include microtubule-associated protein tau and sequences having trinucleotide repeats (e.g., CAG repeats) within the coding region, the expansion of which gives rise to diseases such as Huntington disease (HD), spinocerebellar ataxia 1 (SCA 1), Machado-Joseph disease (MJD/SCA 3), Kennedy disease or spinal and bulbar muscular atrophy (SBMA), and dentatorubraopallidoluysian atrophy (DRPLA). As a non-limiting example, the alternative splicing of exon 10 of tau, which is associated with various neurodegenerative disorders, can be monitored using the reporter constructs of the present invention.

Examples of gene sequences associated with metabolic diseases and disorders include, without limitation, genes expressed in dyslipidemia (e.g., liver X receptors such as LXRα and LXRβ, farnesoid X receptors (FXR), sterol-regulatory element binding protein (SREBP), site-1 protease (S1P), 3-hydroxy-3-methylglutaryl coenzyme-A reductase (HMG coenzyme-A reductase), Apolipoprotein (ApoB), and Apolipoprotein (ApoE)); and diabetes (e.g., glucose 6-phosphatase). See, e.g., Forman et al., *Cell,* 81:687 (1995); Seol et al., *Mol. Endocrinol.,* 9:72 (1995), Zavacki et al., *PNAS USA,* 94:7909 (1997); Sakai et al., *Cell,* 85:1037-1046 (1996); Duncan et al., *J. Biol. Chem.,* 272:12778-12785 (1997); Willy et al., *Genes Dev.,* 9:1033-1045 (1995); Lehmann et al., *J. Biol. Chem.,* 272:3137-3140 (1997); Janowski et al., *Nature,* 383:728-731 (1996); and Peet et al., *Cell,* 93:693-704 (1998).

Non-limiting examples of gene sequences associated with angiogenesis include vascular endothelial growth factor (VEGF) (see, e.g., Reich et al., *Mol. Vis.,* 9:210 (2003)), VEGFR-1/FLT-1, VEGFR-2/FLK-1/KDR (see, e.g., Decaussin et al., *J. Pathol.,* 188: 369-377 (1999), VEGFR-3/FLT-4, endostatin (see, e.g., U.S. Pat. No. 6,174,861), and angiostatin (see, e.g., U.S. Pat. No. 5,639,725).

Examples of gene sequences associated with inflammatory and autoimmune responses include, but are not limited to, cytokines such as growth factors (e.g., TGF-α, TGF-βEGF, FGF, HGF, IGF, NGF, PDGF, CGF, GM-CSF, SCF, etc.), interleukins (e.g., IL-1α, IL-1β, IL-2, IL-4, IL-5, IL-6, IL-7, IL-8, IL-9, IL-10, IL-13, IL-15, IL-17, IL-18, IL-20, IL-23, IL-27, etc.), interferons (e.g., IFN-α, IFN-β, IFN-γ, etc.), TNF-α, Tec family kinases such as Bruton's tyrosine kinase (Btk) (see, e.g., Heinonen et al., *FEBS Lett.,* 527:274 (2002), and Fas and Fas ligand (see, e.g., Song et al., *Nat. Med.,* 9:347 (2003)).

The two-color fluorescent reporter constructs of the present invention are generally introduced into mammalian and other cells using the appropriate vector (e.g., plasmid or virus) either transiently or stably. In transient, or temporary, gene transfer experiments (e.g., transient transfection), plasmid or viral DNA introduced into the host organism does not necessarily integrate into the chromosomes, but can be expressed in the cytoplasm for a short period of time. Expression of a reporter protein of interest, easily monitored by the observation of fluorescence emission using a filter set compatible with the fluorescent protein, usually takes place over a period of several hours after transfection and continues for about 72 to 96 hours after introduction of plasmid DNA into mammalian cells. In certain instances, the plasmid DNA can be incorporated into the genome in a permanent state to form stably transformed cell lines.

In some embodiments, the reporter constructs described herein comprise a vector, such as a plasmid or viral vector, into which a nucleic acid sequence of the invention has been inserted, in a forward or reverse orientation. Preferably, the appropriate DNA sequence is inserted into the vector using any of a variety of procedures known in the art. In general, the DNA sequence is inserted into one or more appropriate restriction endonuclease sites by any procedure known to one of skill in the art.

Any of a variety of vectors are known to one of skill in the art is suitable for use in the present invention. Such vectors are commercially available from many sources, e.g., Qiagen Inc. (Valencia, Calif.), Stratagene (La Jolla, Calif.), and include, but are not limited to, bacterial plasmids (e.g., pQE70, pQE60, pQE-9, pD10, phagescript, psiX174, pBluescript pQE60, pQE-9, pD10, phagescript, psiX174, pBluescript SK, pBluescript KS, pNH8A, pNH16a, pNH18A, pNH46A, ptrc99a, pKK223-3, pKK233-3, pDR540, pRIT5, etc.) and eukaryotic plasmids (e.g., pWLNEO, pSV2CAT, pOG44, pXT1, pSG, pSVK3, pBPV, pMSG, pSVL, etc.). Other vectors include, for example, chromosomal, nonchromosomal, and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). Any other plasmid or vector may be used as long as they are replicable and viable in the host cell or organism.

In some embodiments, mammalian expression vectors comprise an origin of replication, a suitable promoter and enhancer, and also any necessary ribosome binding sites, polyadenylation sites, splice donor and acceptor sites, transcriptional termination sequences, and 5' flanking non-transcribed sequences. In other embodiments, DNA sequences derived from the SV40 splice and polyadenylation sites may be used to provide the non-transcribed genetic elements. Examples of enhancers include, but are not limited to, the SV40 enhancer, the cytomegalovirus early promoter enhancer, the polyoma enhancer, adenovirus enhancers, and the like.

In certain instances, a plasmid useful in fluorescent protein gene transfer experiments comprises several requisite components. For example, the plasmid should contain prokaryotic nucleotide sequences coding for a bacterial replication origin for DNA and an antibiotic resistance gene. These elements, often termed shuttle sequences, allow propagation and selection of the plasmid within a bacterial host to generate sufficient quantities of the vector for transfection into mammalian cells. In addition, the plasmid should contain one or more eukaryotic genetic elements that control the initiation of mRNA transcription, a mammalian polyadenylation signal, an intron (optional), and a gene for co-selection in mammalian cells. Transcription elements are necessary for the mammalian host to express the reporter proteins of interest, and the selection gene is usually an antibiotic that bestows resistance to cells containing the plasmid. These general features vary according to plasmid design, and many vectors have a wide spectrum of additional components suited for particular applications.

In some embodiments, a plasmid or vector of the present invention can include, for example, an expression control sequence operably linked to a nucleic acid sequence encoding one or more reporter proteins to drive reporter gene expression in transfected human and other mammalian cell lines. Suitable expression control sequences include, but are not limited to, promoters such as the human cytomegalovirus (CMV) promoter, the LTR or SV40 promoter, the *E. coli* lac or trp promoter, the phage lambda $P_L$ or $P_R$ promoter, the T3 or T7 promoter, the herpes simplex virus thymidine kinase (HSV-TK) promoter, the mouse metallothionein-I promoter, and other promoter known to control the expression of genes in prokaryotic or eukaryotic cells or their viruses. In other embodiments, a plasmid or vector of the present invention can include an f1 bacteriophage replication origin for single-stranded DNA production. The vector backbone may also contain a simian virus 40 (SV40) replication origin, which is active in mammalian cells that express the SV40 T-antigen. Selection of stable transfectants with the antibiotic G418 can be enabled with a neomycin resistance cassette consisting of the SV40 early promoter, the neomycin resistance gene (aminoglycoside 3'-phosphotransferase), and polyadenylation signals from the herpes simplex virus thymidine kinase (HSV-TK) for messenger stability.

C. Propagation, Isolation, and Transfection of Fluorescent Reporters

In certain embodiments, the present invention provides host cells containing the reporter constructs of the present invention, e.g., in a plasmid or viral DNA vector. The host cell can be a prokaryotic cell (e.g., a bacterial cell) or a eukaryotic cell (e.g., a mammalian, insect, or yeast cell). Specific examples of host cells include, but are not limited to, *Escherichia coli, Salmonella typhimurium, Bacillus subtilis*, and various species within the genera *Pseudomonas, Streptomyces*, and *Staphylococcus*, as well as *Saccharomycees cerivisiae, Schizosaccharomycees pombe, Drosophila* S2 cells, *Spodoptera* Sf9 cells, Chinese hamster ovary (CHO) cells, COS-7 lines of monkey kidney fibroblasts, and the C127, 3T3, 293, 293T, HeLa, MDCK, and BHK cell lines.

Successful mammalian transfection experiments generally rely on the use of high quality plasmid or viral DNA vectors that are relatively free of bacterial endotoxins. In certain instances, high quality plasmid or viral DNA can be purified using cesium chloride density gradient centrifugation in the presence of an intercalation agent (e.g., ethidium bromide or propidium iodide). In certain other instances, high quality plasmid or viral DNA can be prepared using ion-exchange column chromatography methods (e.g., "mini-preps") to yield large quantities of endotoxin-free DNA in a relatively short period of time.

Specialized bacterial mutants, termed competent cells, have been developed for convenient and relatively cheap amplification of plasmid vectors. In general, the bacterial strain contains a palette of mutations that render them particularly susceptible to plasmid replication, and have been chemically permeabilized for transfer of the DNA across the membrane and cell wall in a procedure known as transformation. After transformation, the bacteria are grown to logarithmic phase in the presence of the selection antibiotic dictated by the plasmid. The bacterial culture can be concentrated by centrifugation and disrupted by lysis with an alkaline detergent solution containing enzymes to degrade contaminating RNA. The lysate is then filtered and placed on the ion-exchange column. Unwanted materials, including RNA, DNA, and proteins, are thoroughly washed from the column before the plasmid DNA is eluted using a high salt buffer. Alcohol (e.g., isopropanol) precipitation concentrates the eluted plasmid DNA, which is collected by centrifugation, washed, and redissolved in buffer. The purified plasmid DNA can be used in transfection experiments.

Mammalian cells used for transfection should typically be in excellent physiological condition and growing in logarithmic phase during the procedure. A wide spectrum of transfection reagents has been commercially developed to optimize uptake of plasmid DNA by cultured cells. These techniques range from calcium phosphate precipitation to lipofection, which involves the sequestering of plasmid DNA in lipid vesicles that fuse to the cell membrane and deliver the contents to the cytoplasm. Other methods for introducing the reporter constructs of the present invention into host cells include, but are not limited to, DEAE-Dextran mediated transfection, electroporation, and the like. Electroporation, for example, applies short, high voltage pulses to a cellular suspension to induce pore formation in the plasma membrane, subsequently allowing the transfection DNA to enter the cell, and has proven to generate stable cell lines with linearized plasmids and purified genes.

D. Screening Methods

In some aspects, the fluorescent reporter constructs of the present invention can be used in a screening assay (e.g., high-throughput screen) for compounds that affect alternative pre-mRNA splicing. In certain instances, compounds which modulate the alternative splicing of genes associated with tumorigenesis and cell transformation find use in inhibiting the growth of and promoting the regression of a tumor, for example, renal cell carcinoma, bladder cancer, prostate cancer, testicular cancer, ovarian cancer, cervical cancer, lung cancer, breast cancer, colon cancer, stomach cancer, head and neck cancer, brain cancer, leukemias, B-cell lymphomas (e.g., non-Hodgkin's lymphomas, including Burkitt's, Small Cell, and Large Cell lymphomas), hepatocarcinoma, and multiple myeloma. The identified compounds can inhibit cancer growth or progression alone, or when used in combination with other cancer therapies, including chemotherapies, radiation therapies, hormonal therapies, immunotherapies, and combinations thereof. In certain other instances, compounds which modulate the alternative splicing of genes associated with neurodegenerative disorders find use in treating, delaying, or preventing, for example, spinal muscular atrophy (SMA), myotonic dystrophy, spinal cerebellar ataxia (SCA), fragile X syndrome, frontotemporal dementia with Parkinsonism linked to chromosome 17 (FTPD-17), autism, and severe combined immunodeficiency disease (SCID).

Using the assays described herein, one of skill in the art can identify lead compounds that are suitable for further testing to identify those that are therapeutically effective modulating agents by screening a variety of compounds and mixtures of compounds for their ability to affect alternative splicing of one or more exons of interest. Compounds of interest can be either synthetic or naturally-occurring.

Screening assays can be carried out in vitro or in vivo. Typically, initial screening assays are carried out in vitro, and can be confirmed in vivo using cell-based assays or animal models. For instance, a compound that changes the level of the two fluorescent reporter proteins expressed from a reporter system of the present invention (e.g., RFP/GFP expression ratio) in comparison to cells unexposed to the compound can be identified and selected as a modulator of alternative splicing using the screening assays described herein.

The screening methods are designed to screen large chemical or polymer (e.g., inhibitory RNA, including siRNA and antisense RNA, peptides, polynucleotides, small organic molecules, etc.) libraries by automating the assay steps and providing compounds from any convenient source to the assays, which are typically run in parallel (e.g., in microtiter formats on microtiter plates in robotic assays).

The present invention also provides in vitro assays in a high-throughput format. In the high-throughput assays of the present invention, it is possible to screen up to several thousand different compounds in a single day. In particular, each well of a microtiter plate can be used to run a separate assay against a selected potential compound, or, if concentration or incubation time effects are to be observed, every 5-10 wells can test a single compound. Thus, a single standard microtiter plate can assay about 100 (96) compound. If 1536-well plates are used, then a single plate can easily assay from about 100 to about 1500 different compounds. It is possible to assay many different plates per day; assay screens for up to about 6000-20,000, and even up to about 100,000-1,000,000 different compounds are possible using the integrated systems of the present invention. The steps of labeling, addition of reagents, fluid changes, and/or detection are compatible with full automation, for instance, using programmable robotic systems or "integrated systems" commercially available, for example, through BioTX Automation (Conroe, Tex.), Qiagen, Inc. (Valencia, Calif.), Beckman Coulter (Fullerton, Calif.), and Caliper Life Sciences (Hopkinton, Mass.).

Essentially, any chemical compound can be tested as a potential modulator of alternative splicing for use in the screening methods of the present invention. Most preferred are generally compounds that can be dissolved in aqueous or organic (especially DMSO-based) solutions. It will be appreciated that there are many suppliers of chemical compounds, including Sigma-Aldrich (St. Louis, Mo.) and Fluka Chemika-Biochemica Analytika (Buchs Switzerland), as well as providers of small organic molecule and peptide libraries ready for screening, including Chembridge Corp. (San Diego, Calif.), Discovery Partners International (San Diego, Calif.), Triad Therapeutics (San Diego, Calif.), Nanosyn (Menlo Park, Calif.), Affymax (Palo Alto, Calif.), ComGenex (South San Francisco, Calif.), and Tripos, Inc. (St. Louis, Mo.).

In some embodiments, modulators of alternative splicing are identified by screening a combinatorial library containing a large number of potential therapeutic compounds (potential modulator compounds). Such "combinatorial chemical or peptide libraries" can be screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

The preparation and screening of combinatorial chemical libraries is well known to those of skill in the art (see, e.g., Beeler et al., *Curr Opin Chem. Biol.*, 9:277 (2005); and Shang et al., *Curr Opin Chem. Biol.*, 9:248 (2005)). Libraries of use in the present invention can be composed of amino acid compounds, nucleic acid compounds, carbohydrates, or small organic compounds. Carbohydrate libraries have been described in, for example, Liang et al., *Science*, 274:1520-1522 (1996); and U.S. Pat. No. 5,593,853.

Representative amino acid compound libraries include, but are not limited to, peptide libraries (see, e.g., U.S. Pat. Nos. 5,010,175; 6,828,422; and 6,844,161; Furka, *Int. J. Pept. Prot. Res.*, 37:487-493 (1991); Houghton et al., *Nature*, 354: 84-88 (1991); and Eichler, *Comb Chem High Throughput Screen.*, 8:135 (2005)), peptoids (PCT Publication No. WO 91/19735), encoded peptides (PCT Publication No. WO 93/20242), random bio-oligomers (PCT Publication No. WO 92/00091), vinylogous polypeptides (Hagihara et al., *J. Amer. Chem. Soc.*, 114:6568 (1992)), nonpeptidal peptidomimetics with β-D-glucose scaffolding (Hirschmann et al., *J. Amer. Chem. Soc.*, 114:9217-9218 (1992)), peptide nucleic acid libraries (see, e.g., U.S. Pat. No. 5,539,083), antibody libraries (see, e.g., U.S. Pat. Nos. 6,635,424 and 6,555,310; PCT Application No. PCT/US96/10287; and Vaughn et al., *Nature Biotechnology*, 14:309-314 (1996)), and peptidyl phosphonates (Campbell et al., *J. Org. Chem.*, 59:658 (1994)).

Representative nucleic acid compound libraries include, but are not limited to, genomic DNA, cDNA, mRNA, inhibitory RNA (e.g., RNAi, siRNA), and antisense RNA libraries. See, e.g., Ausubel, *Current Protocols in Molecular Biology*, eds. 1987-2005, Wiley Interscience; and Sambrook and Russell, *Molecular Cloning: A Laboratory Manual*, 2000, Cold Spring Harbor Laboratory Press. Nucleic acid libraries are described in, for example, U.S. Pat. Nos. 6,706,477; 6,582, 914; and 6,573,098. cDNA libraries are described in, for example, U.S. Pat. Nos. 6,846,655; 6,841,347; 6,828,098; 6,808,906; 6,623,965; and 6,509,175. RNA libraries, for example, ribozyme, RNA interference, or siRNA libraries, are described in, for example, Downward, *Cell*, 121:813 (2005) and Akashi et al., *Nat. Rev. Mol. Cell. Biol.*, 6:413 (2005). Antisense RNA libraries are described in, for example, U.S. Pat. Nos. 6,586,180 and 6,518,017.

Representative small organic molecule libraries include, but are not limited to, diversomers such as hydantoins, benzodiazepines, and dipeptides (Hobbs et al., *Proc. Nat. Acad. Sci. USA*, 90:6909-6913 (1993)); analogous organic syntheses of small compound libraries (Chen et al., *J. Amer. Chem. Soc.*, 116:2661 (1994)); oligocarbamates (Cho et al., *Science*, 261:1303 (1993)); benzodiazepines (e.g., U.S. Pat. No. 5,288, 514; and Baum, *C&EN*, January 18, page 33 (1993)); isoprenoids (e.g., U.S. Pat. No. 5,569,588); thiazolidinones and metathiazanones (e.g., U.S. Pat. No. 5,549,974); pyrrolidines (e.g., U.S. Pat. Nos. 5,525,735 and 5,519,134); morpholino compounds (e.g., U.S. Pat. No. 5,506,337); tetracyclic benzimidazoles (e.g., U.S. Pat. No. 6,515,122); dihydrobenzpyrans (e.g., U.S. Pat. No. 6,790,965); amines (e.g., U.S. Pat. No. 6,750,344); phenyl compounds (e.g., U.S. Pat. No. 6,740,712); azoles (e.g., U.S. Pat. No. 6,683,191); pyridine carboxamides or sulfonamides (e.g., U.S. Pat. No. 6,677,452); 2-aminobenzoxazoles (e.g., U.S. Pat. No. 6,660,858); isoindoles, isooxyindoles, or isooxyquinolines (e.g., U.S. Pat. No. 6,667,406); oxazolidinones (e.g., U.S. Pat. No. 6,562,844); and hydroxylamines (e.g., U.S. Pat. No. 6,541,276).

Devices for the preparation of combinatorial libraries are commercially available. See, e.g., 357 MPS and 390 MPS from Advanced Chem. Tech (Louisville, Ky.), Symphony from Rainin Instruments (Woburn, Mass.), 433A from Applied Biosystems (Foster City, Calif.), and 9050 Plus from Millipore (Bedford, Mass.).

As a non-limiting example, a high-throughput screen for small molecules that alter the splicing of an alternative cassette exon can be performed according to the following procedure: An exon of interest including about 50-100 nucleotides of each of the flanking introns is cloned into a vector comprising the reporter construct of the present invention by insertion into the start codon of the nucleic acid sequence encoding the first reporter protein (e.g., using EcoRI and BamHI restriction sites present in the reporter intron). The vector is linearized (e.g., using DraIII) and transfected into adherent mammalian cells. Cell clones stably expressing the vector are selected using Geneticin (G418). A stable cell clone that is expressing the reporter is expanded and plated at a density of about 2000-6000 cells per well in 384-well plates. The cells are incubated for about 2-4 hours to allow them to attach to the surface of the plates. A chemical library comprising small molecules is applied to the plates and the cells are incubated for an additional 6-48 hours. After the incubation is complete, the media is removed and the cells are lysed in the wells using RIPA buffer (1% Nonidet P-40, 1% sodium deoxycholate, 0.1% SDS, 150 mM NaCl, 10 mM sodium phosphate (pH 7.2), 2 mM EDTA, 50 mM NaF, 5 mM beta-glycerophosphate). The fluorescence of the reporter proteins is measured, for example at 510 nm for green fluorescent protein and 610 nm for red fluorescent protein after excitation at 485 and 580 nm, respectively. After background subtraction, the logarithm (base 2) is calculated for the ratio of the red to the green fluorescence (log-ratio) and for the product of the two fluorescence intensities (log-expression). The log-ratios are normalized by Lowess regression using the log-expression as an independent variable. The normalized ratios of the library components are compared to the ratios of the control samples. Dose response experiments are performed for the identified compounds with log ratios which deviate significantly from the controls to determine the optimal concentrations. The effect of the selected compounds on splicing can be verified by RT-PCR on the minigene (i.e., reporter construct) as well as on the endogenous splicing event.

E. Kits of the Invention

The present invention also provides kits to facilitate and/or standardize the use of the compositions provided herein, as well as to facilitate the methods described herein. Materials and reagents to carry out these various methods can be provided in kits to facilitate execution of the methods. As used herein, the term "kit" includes a combination of articles that facilitates a process, assay, analysis, or manipulation. In particular, kits comprising the fluorescent reporter constructs of the present invention find utility in a wide range of applications including basic research, drug screening, and drug design.

Kits can contain chemical reagents (e.g., polynucleotides or polypeptides) as well as other components. In addition, the kits of the present invention can include, without limitation, instructions to the kit user (e.g., directions for introducing the reporter construct into a cell, directions for detecting the expression of the fluorescent reporter proteins, etc.), apparatus and reagents for sample collection and/or purification, apparatus and reagents for product collection and/or purification, reagents for bacterial cell transformation, reagents for eukaryotic cell transfection, previously transformed or transfected host cells, sample tubes, holders, trays, racks, dishes, plates, solutions, buffers or other chemical reagents, suitable samples to be used for standardization, normalization, and/or control samples. Kits can also include cells transfected with the reporter construct of the invention, as well as controls, e.g., cells transfected with control constructs. Kits of the present invention can also be packaged for convenient storage and safe shipping, for example, in a box having a lid.

In some embodiments, the kits can provide a polynucleotide vector (e.g., a plasmid) comprising a reporter construct of the present invention, cell strains suitable for propagating the vector, and instructions to the kit user.

IV. Examples

The following examples are offered to illustrate, but not to limit, the claimed invention.

Example 1

Two-Color Fluorescent Reporter Constructs

This example illustrates several embodiments of the two-color fluorescent reporter and control reporter constructs of the present invention.

Test Fluorescent Reporter Constructs

FIG. 1A shows an exemplary two-color fluorescent reporter construct of the present invention. The reporter construct comprises a promoter (100) operably linked to a nucleic acid sequence encoding GFP (e.g., EGFP) as a first reporter protein and RFP (e.g., DsRED-Express) as a second reporter protein. The GFP start codon is interrupted between the "A" and "T" nucleotides by a reporter intron carrying EcoRI and BamHI restriction sites (SEQ ID NO:2). As a result, the nucleic acid sequence encoding GFP is divided into (1) a first exon (110) ending in the "A" nucleotide of the GFP start codon (SEQ ID NO:3); and (2) a second exon (120) which begins at the "T" nucleotide of the GFP start codon and comprises the remainder of the GFP sequence. The GFP sequence can be a modified EGFP sequence carrying mutations designed to eliminate internal ATG codons or the Kozak consensus sequences surrounding them (SEQ ID NO:4). The GFP sequence can further comprise a modified mouse ornithine decarboxylase (MODC) PEST sequence at the 3' end (SEQ ID NO:5) that carries silent mutations and amino acid changes to eliminate internal ATG codons and to decrease its homology to the wild-type sequence. The second exon further comprises the RFP sequence (130), e.g., destabilized DsRED-Express (SEQ ID NO:6), downstream of the GFP and PEST sequences. The RFP sequence can further comprise a PEST sequence at the 3' end. A cassette comprising an exon of interest (140), e.g., "G . . . NNN . . . G", wherein "G" represents the first and last consensus nucleotides of the exon and "NNN" represents the remaining sequence of the exon, flanked by two introns is inserted into the EcoRI and BamHI restriction sites of the reporter intron.

In an alternative embodiment, the reporter construct can comprise a promoter operably linked to a nucleic acid sequence encoding YFP (e.g., EYFP), CFP (e.g., ECFP), or BFP as a first reporter protein and RFP (e.g., DsRED-Express) as a second reporter protein. The start codon of the first reporter protein is interrupted between the "A" and "T" nucleotides by a reporter intron carrying EcoRI and BamHI restriction sites (SEQ ID NO:2). As a result, the nucleic acid sequence encoding the first reporter protein is divided into (1) a first exon ending in the "A" nucleotide of the start codon of the first reporter protein (SEQ ID NO:3); and (2) a second exon which begins at the "T" nucleotide of the start codon and comprises the remainder of the first reporter sequence. The first reporter sequence can be a modified sequence carrying mutations designed to eliminate internal ATG codons or the Kozak consensus sequences surrounding them (see, e.g., the modified EYFP sequence set forth in SEQ ID NO:7). The first reporter sequence can further comprise a modified PEST sequence at the 3' end (SEQ ID NO:5) that carries silent mutations and amino acid changes to eliminate internal ATG codons and to decrease its homology to the wild-type sequence. The second exon further comprises the RFP sequence downstream of the first reporter and PEST sequences. The RFP sequence can further comprise a PEST sequence at the 3' end. A cassette comprising an exon of interest flanked by two introns is inserted into the EcoRI and BamHI restriction sites of the reporter intron.

Table 2 shows modifications which can be made to the EGFP/EYFP/ECFP/BFP nucleic acid sequences to eliminate internal ATG codons and the Kozak consensus sequences surrounding them. Table 3 shows modifications which can be made to the PEST nucleic acid sequence to eliminate internal ATG codons and to prevent recombination between PEST sequences.

TABLE 2

| Nucleotide substitution | Amino acid change | Comment |
| --- | --- | --- |
| T110C | Silent | Out of frame ATG to ATC; Eliminates BcgI site |
| A234C | M79L | |
| T258A, C259G, C260T, C263A | Silent | Eliminates Kozak consensus in front of M89 |
| T460C, G461C | M154T | |
| C653T | Silent | Eliminates Kozak consensus in front of M219 |
| T700C, G701C | M234T | |

TABLE 3

| Nucleotide substitution | Amino acid change | Comment |
| --- | --- | --- |
| A58G, G84C | M→V, M→L | |
| C78T, C87T, C88A, T90A, C93T, T96A, A99C, T105C, T108C, T111C, T114C, G117A, C120T, T123C, G126C | Silent | These mutations are located in the first reporter PEST sequence. |
| T12C, T42C, T45C | Silent | Out of frame ATG to ACG |

The nucleotide position is relative to the beginning of the PEST sequence.

There are 3 types of mRNAs that can be generated by alternative splicing from a reporter construct comprising a nucleic acid sequence encoding GFP as a first reporter protein and RFP as a second reporter protein:

1. mRNAs that retain one or both introns or utilize cryptic splice sites. These mRNAs will not express either GFP or RFP.
2. mRNAs where the entire cassette, including both the alternative exon and introns, has been spliced out, thereby regenerating the GFP start codon (150). These mRNAs will express the GFP protein and can be detected by fluorescence in the green part of the spectrum, e.g., excitation at 484 nm and emission at 507 nm.
3. mRNAs where the two introns have been spliced out, but which retain the alternative cassette exon (160). These mRNAs will express the downstream ORF that encodes RFP. The presence of these mRNAs can be detected by fluorescence in the red part of the spectrum, e.g., excitation at 555 nm and emission at 584 nm.

The reporter construct described above was tested using three artificial alternative exons (Dup34, Dup51, and Dup51Bcg) that exhibit different exon inclusion levels. The fluorescence was monitored by microscopy and the splicing pattern of each exon was verified by RT-PCR. All three exons generated the expected GFP and RFP levels. Dup34, which was almost completely skipped, resulted in high levels of GFP and low levels of RFP; Dup51 was included in approximately 60% of the mRNA, resulting in moderate GFP and RFP levels; and Dup51Bcg was included in the majority of the mRNA, thereby producing high levels of RFP and low levels of GFP.

FIG. 1B shows a two-color fluorescent reporter construct of the present invention in which the GFP start codon is interrupted by a cassette comprising exon 10 of the human tau gene flanked by two introns. Exon 10 encodes one of four microtubule-binding domains in tau and is normally only partially included, resulting in tau isoforms with either three or four microtubule-binding domains. Cis-acting mutations that increase tau exon 10 splicing have been associated with the inherited disorder frontotemporal dementia with Parkinsonism linked to chromosome 17. A stable cell line carrying the reporter construct with tau exon 10 showed the expected high GFP and low RFP levels. The splicing pattern of the exon was tested by RT-PCR.

FIG. 1C shows an alternative two-color fluorescent reporter construct of the present invention. For example, an alternative exon that contains an "A" nucleotide at its 3' end or strong translation start codons can be analyzed with a modified reporter construct in which inclusion of the alternative exon results in GFP synthesis, while alternative exon skipping produces RFP. As shown in FIG. 1C, the nucleic acid sequence encoding GFP is divided into (1) a first exon ending in a "G" nucleotide (SEQ ID NO:8); and (2) a second exon which begins at the "TG" nucleotides of the GFP start codon and comprises the remainder of the GFP sequence. Inclusion of an alternative exon that contains an "A" nucleotide at its 3' end produces a start codon and results in GFP expression, whereas RFP is expressed when the alternative exon is spliced out. Other modifications are possible that will allow a vector comprising the reporter construct to be used for the study of exons that start with "TG" nucleotides and are in the same reading frame as the GFP reporter. The reporter construct can also be adapted to certain alternative 5' and 3' splice sites or mutually exclusive exons.

Control Fluorescent Reporter Constructs

Figure 2:
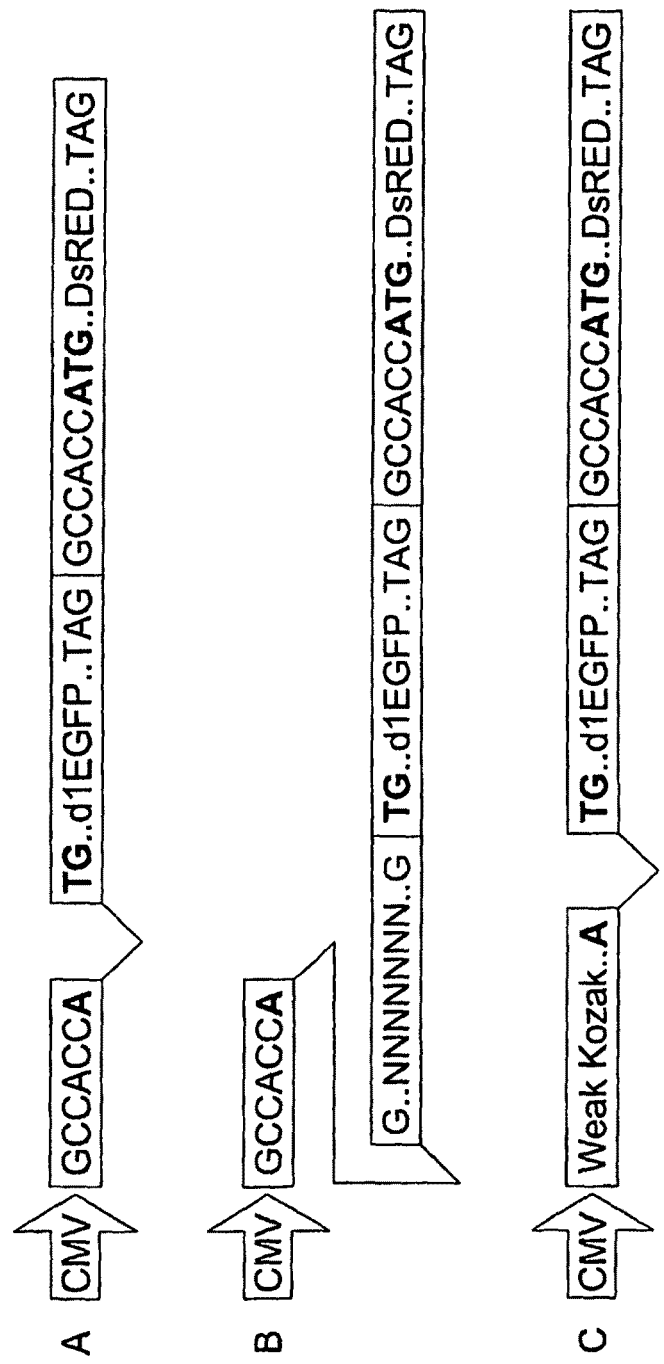
FIG. 2 shows several embodiments of the control single intron reporter constructs of the present invention.

The two spliced mRNAs generated from the reporter construct differ in the size of their 5' untranslated regions (5'-UTRs). This can lead to the discovery of compounds that modulate the processivity with which the ribosome scans the mRNA for start codons. To separate the effect on splicing from the effect on initiation of translation, control experiments can be performed using two single intron reporters (FIG. 2). The two control reporter constructs can be derived from the splicing reporter construct by deleting the alternative exon and one of the introns (FIG. 2A) or a single intron (FIG. 2B). When co-transfected, the first control reporter produces mRNA that lacks the alternative exon and the second reporter produces mRNA containing the alternative exon. The levels of the two mRNAs do not depend on alternative splicing and the amount of the expressed protein is dependent only on the ability to initiate translation after a long or short untranslated region. Alternatively, a single reporter derived from the control reporter construct shown on FIG. 2A can be used. In one embodiment, the sequence around of the GFP start codon can be mutated to weaken its similarity to the Kozak consensus sequence (FIG. 2C).

Example 2

Screen for Small Molecules that Alter the Splicing of Tau Exon 10

This example illustrates the establishment of a stable cell line which expresses a two-color fluorescent reporter construct having a cassette comprising exon 10 of the human tau gene flanked by introns inserted into the start codon of the GFP open reading frame. This example also illustrates a method for subtracting background fluorescence to increase the dynamic range of the reporter construct. This example further illustrates a high-throughput small molecule screen for identifying compounds that modulate alternative splicing.

Stable Cell Lines

Exon 10 of the human tau gene (SEQ ID NO:9; see also, GenBank Accession No. AF027494) containing short stretches (about 50-100 nucleotides) of each of the flanking introns (i.e., intronic sequences from introns 9 and 10; see, e.g., Wang et al., *J. Neurochem.*, 88:1078-1090 (2004)) was cloned into the EcoRI and BamHI restriction sites of the reporter intron (SEQ ID NO:2), which interrupts the start codon of the GFP open reading frame. The clone was linearized using DraIII and transfected into adherent mammalian cells.

Figure 3:
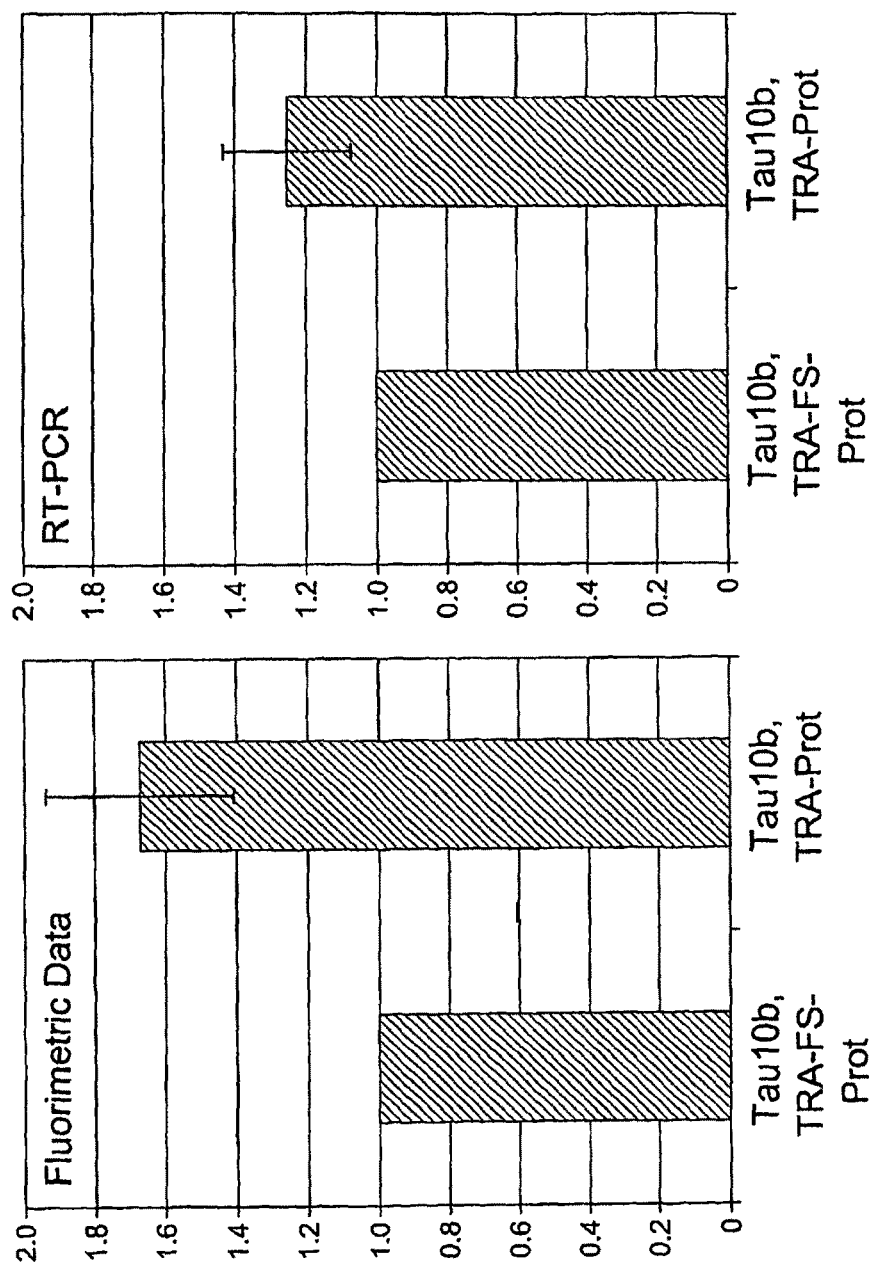
FIG. 3 shows bar plots illustrating the inclusion of tau exon 10 (Tau10b) into the mRNA from stable cell lines relative to control cells. The reporter construct carrying Tau10b was co-transfected with a Tra2-beta expressing construct (TRA-Prot) and compared to cells that did not express Tra2-beta (TRA-FS-Prot). Both the fluorimetric assay (left panel) and the RT-PCR assay (right panel) detected an increase in the inclusion of Tau10b when Tra2-beta protein was present in the cells.

To verify that the clones can faithfully recreate the splicing of wild-type tau exon 10, the cells were co-transfected with Tra2-beta, a known regulator of tau exon 10 splicing. As shown in FIG. 3, both fluorimetric and RT-PCR assays detected an increase in the inclusion of exon 10 in the mRNA transcript compared to control clones. The clones expressing both the reporter construct and Tra2-beta were used to generate stable cell lines. The expression of the reporter proteins in the stable cell lines was verified by fluorescence microscopy.

Background Subtraction and Dynamic Range

Figure 4A:
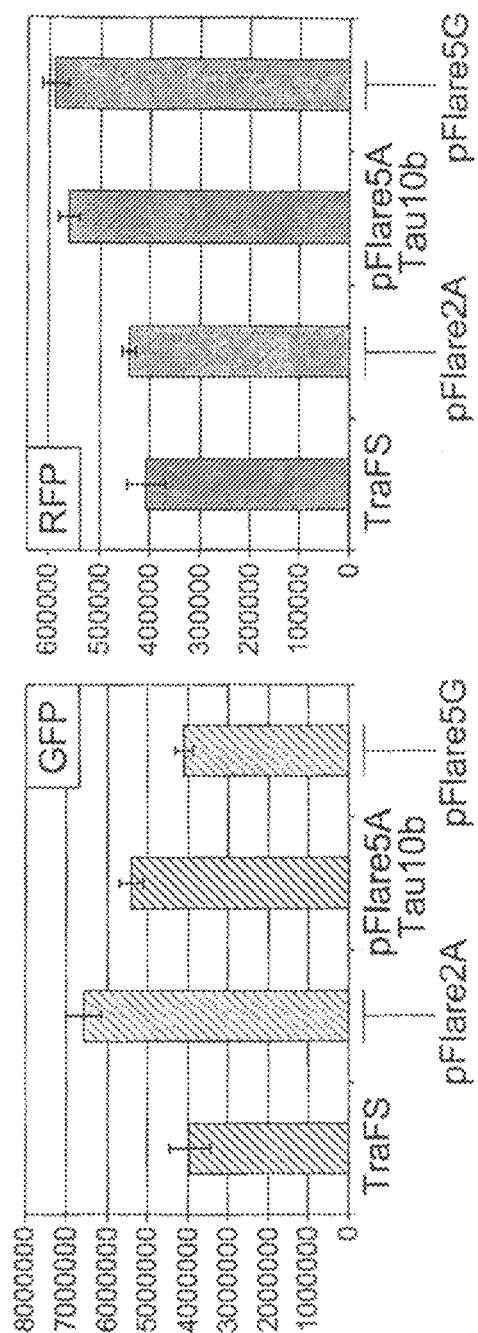
FIG. 4 shows the background subtraction of a two-color fluorescent reporter construct of the present invention. Panel A illustrates a typical read (relative fluorescence units) without background subtraction. TraFS is a non fluorescent control, pFlare2A is an empty vector which produces high levels of GFP, pFlare5A Tau10b carries tau exon 10, and pFlare5G is an empty vector in which the last nucleotide of the first exon is changed to G so RFP is expressed instead of GFP. Panel B illustrates the signal (in relative fluorescence units) obtained after background subtraction. Panel C shows the structure of the pFlare2A and pFlare5G vectors. The structure of pFlare5A Tau10b is provided in FIG. 1B.

Although the fluorimetric assay exhibited high background levels due to auto-fluorescence of the cells and culture media, the signal to noise ratio was lowered when the assay was scaled to 384-well plates for high-throughput screening, where only 2000 to 10,000 cells were present in each well. Since the fluorescence of some of the compounds screened could increase the background fluorescence by an order of magnitude, the background was calculated and subtracted for each well. In particular, the background was calculated by measuring the fluorescence of each channel after excitation with shorter wavelengths than the optimal for the reporter proteins. This measurement was corrected using data from non-reporter cells before being subtracted from the reporter-expressing cells as background. The following formulas describe the background subtraction procedure:

$$GFP = F_{485/510} - \frac{F_{425/510} * NF_{485/510}}{NF_{425/510}}$$

$$RFP = F_{580/610} - \frac{F_{548/610} * NF_{580/610}}{NF_{548/610}},$$

wherein GFP and RFP are the corrected fluorescence intensity values for the GFP and RFP reporter proteins; $F_{X/Y}$ is the emission at Ynm after excitation at Xnm of cells expressing the fluorescent reporter, and $NF_{X/Y}$ is the fluorescence of cells that do not express the reporter. The results from the background subtraction are shown in FIG. 4.

Figure 4B:
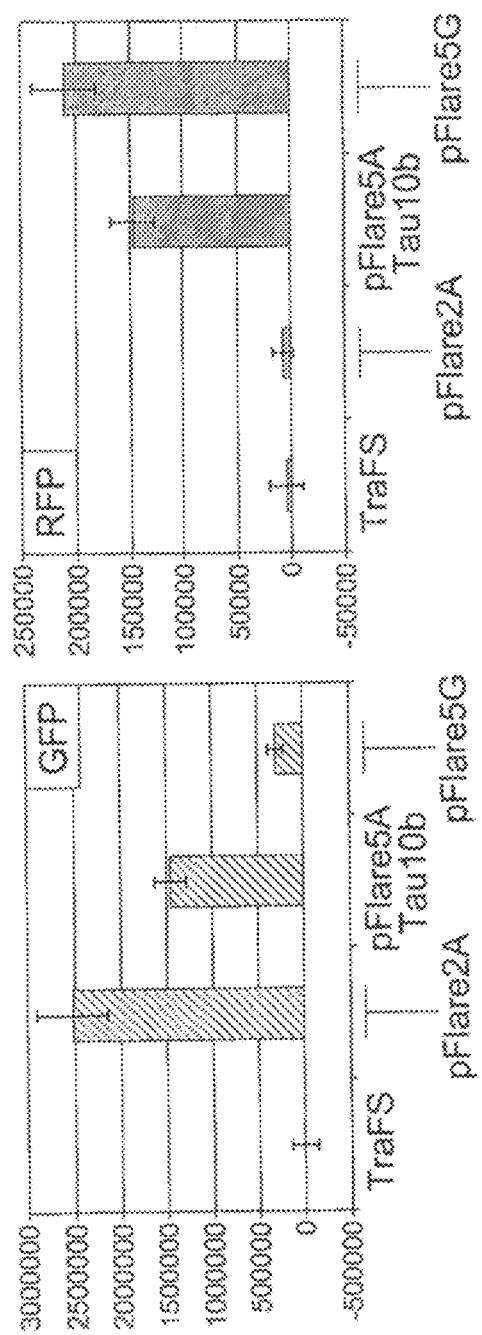
Figure 4C:
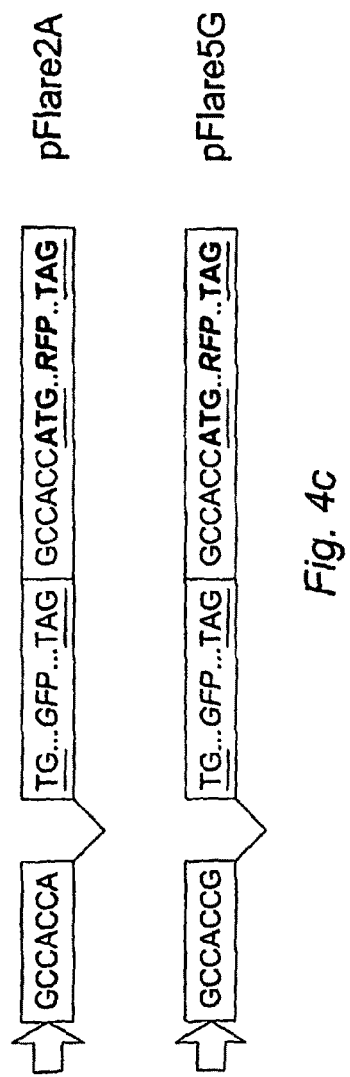
Figure 5:
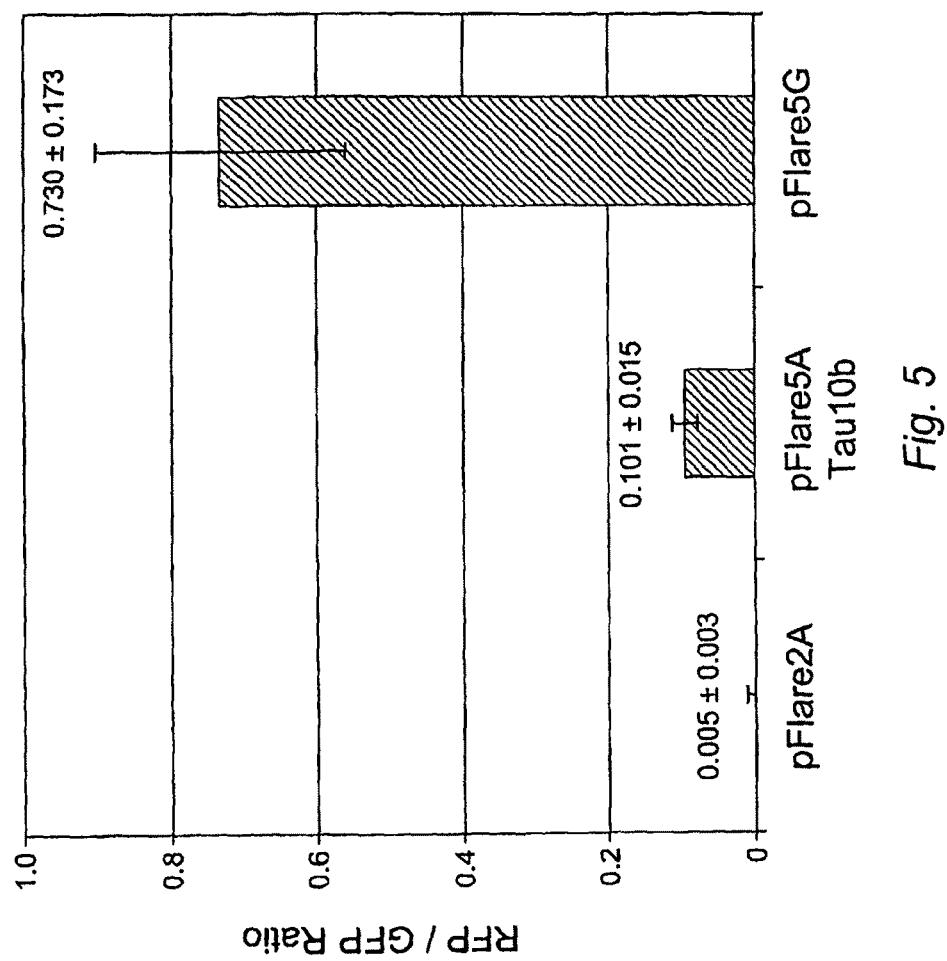
FIG. 5 shows the dynamic range of a two-color fluorescent reporter construct of the present invention. Ratios of RFP to GFP fluorescence intensity were calculated for the reporters shown in FIG. 4. The pFlare 2A and pFlare5G vectors produce the maximum GFP and RFP levels, respectively, that can be generated by the reporter. The two vectors were used to determine the end points of the dynamic range of the reporter. Measuring the RFP to GFP ratio resulted in more than a 100 fold difference between the two clones. The numbers above the bars indicate the average of 6 experiments +/− the standard deviation.

As shown in FIG. 4B, after background subtraction there is approximately a 10 to 20 fold difference between the maximum and minimum values in each channel. Because the reporter construct generates different fluorescent proteins depending on the splicing event, alternative exon inclusion can be measured by calculating the ratio of RFP to GFP. As such, the dynamic range comprises the product of the dynamic ranges of the individual reporter proteins, resulting in an approximately 150 fold difference in the RFP to GFP ratios of pFlare2A and pFlare5G (FIG. 5).

High-Throughput Screening

Figure 6A:
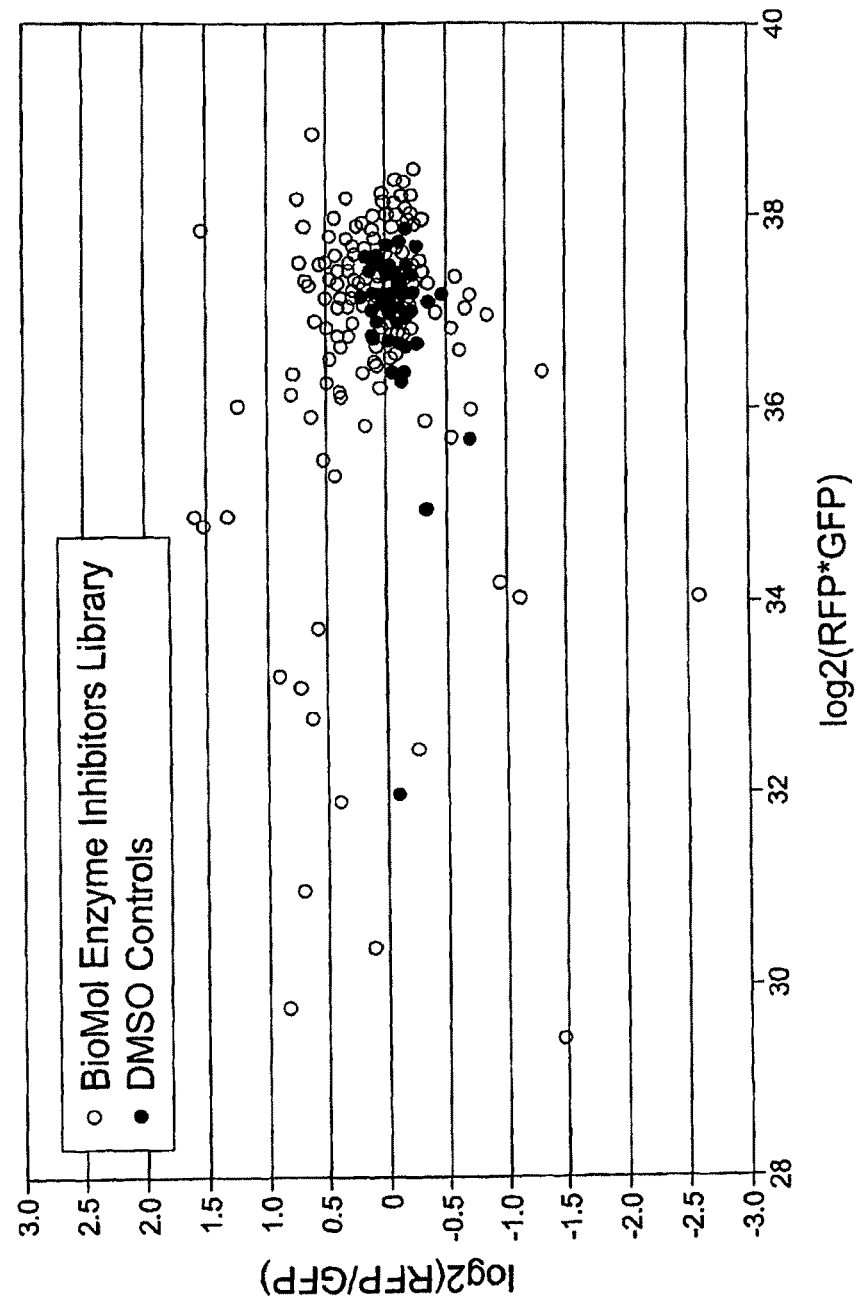
FIG. 6 shows log-ratio to log-expression plots obtained from high-throughput screens using a two-color fluorescent reporter construct of the present invention. Two libraries were screened using the reporter construct carrying exon 10 of the human tau gene. The overall expression levels (log 2(RFP*GFP)) were plotted against the relative exon inclusion (log 2(RFP/GFP)). The data were normalized using Lowess scatterplot smoothing. The DMSO controls clustered with the majority of the tested compounds. Compounds that altered the overall expression levels were clearly distinguished from compounds that changed the RFP to GFP ratio by their displacement along different axes.
Figure 6B:
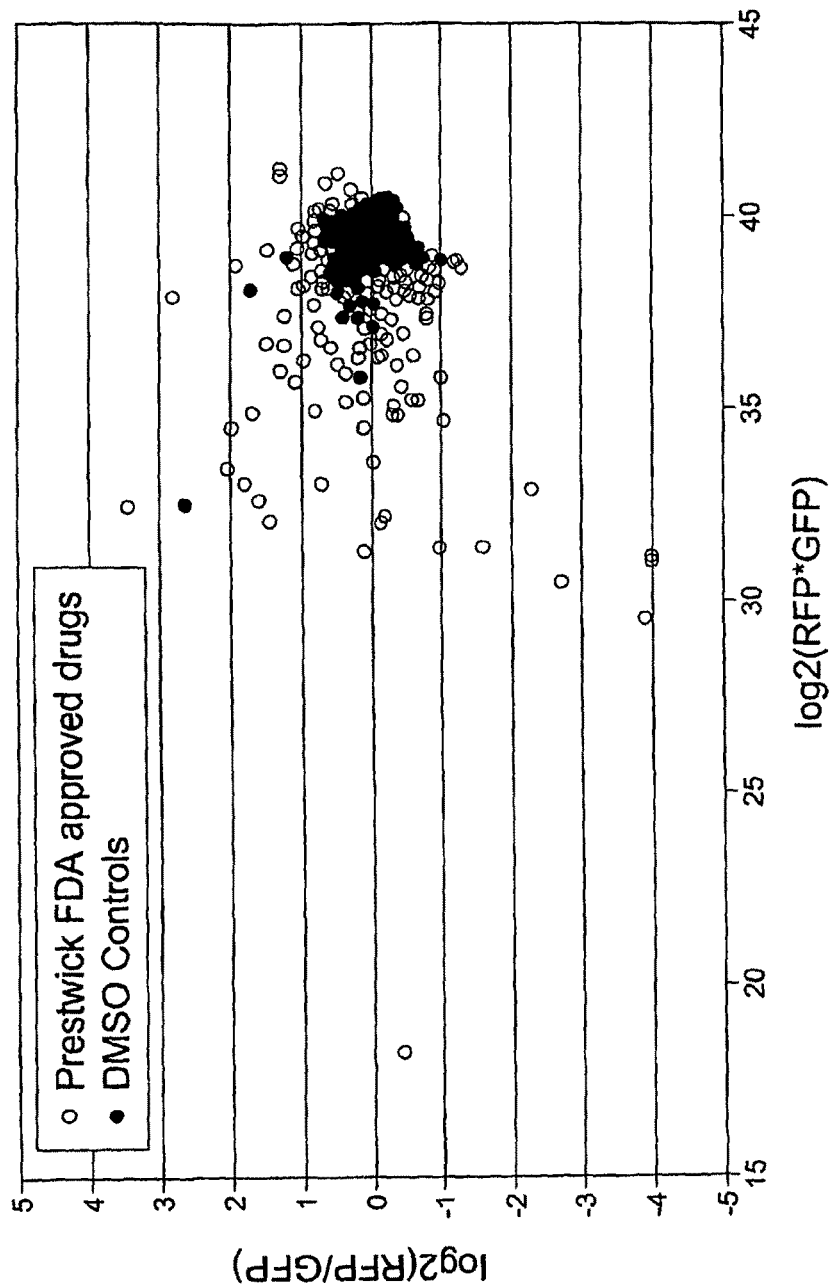

The two-color fluorescent reporter constructs described above carrying exon 10 of the human tau gene were used in high-throughput small molecule screens of a library of enzyme inhibitors (FIG. 6A) and a library of FDA approved drugs (FIG. 6B). The stable cell line was plated at density of 5000 cells per well in 384-well plates. HEK 293 cells to be used as the non-fluorescent control for background subtraction were plated in separate plates at the same density. Each library was applied to the plates and the cells were incubated for 16 hours. The media was removed and the cells were lysed in RIPA buffer (1% Nonidet P-40, 1% sodium deoxycholate, 0.1% SDS, 150 mM NaCl, 10 mM sodium phosphate (pH 7.2), 2 mM EDTA, 50 mM NaF, 5 mM beta-glycerophosphate). The fluorescence intensities were measured using an Analyst AD plate reader. The background was subtracted as described above and the logarithm at base 2 was calculated for the ratio of RFP to GFP fluorescence intensities (log-ratio) and the product of the GFP and RFP fluorescence intensities (log-expression) for each data point. The log-ratios were normalized by Lowess regression using the log-expression as an independent variable.

Figure 7:
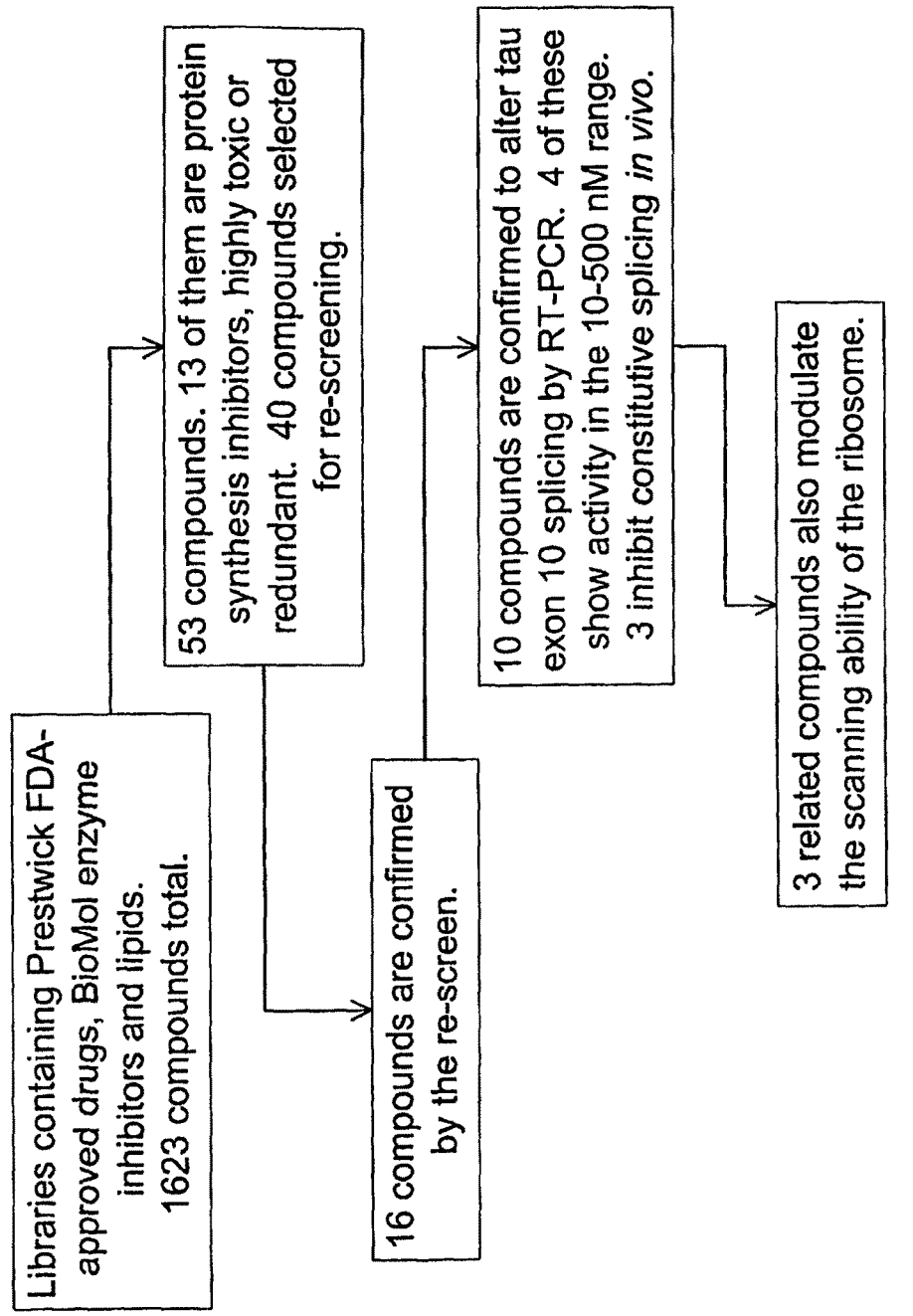
FIG. 7 provides a flowchart summarizing the results of high-throughput small molecule screens for compounds that alter the alternative splicing of exon 10 of the human tau gene.

As shown in FIG. 6, both screens identified several compounds that significantly changed the ratio of RFP to GFP fluorescence intensity compared to the DMSO controls. Apparent were compounds that decreased the overall expression levels (log 2-expression<35), without significantly changing tau exon 10 inclusion levels. FIG. 7 provides a flowchart summarizing the results of high-throughput small molecule screens for compounds that alter the alternative splicing of exon 10 of the human tau gene. Table 4 shows the 28 compounds identified from the enzyme inhibitor screen that deviated significantly from DMSO controls.

TABLE 4

| Log-ratio | Standard deviation | Compound | Activity |
|---|---|---|---|
| −1.72 | 0.74 | CANTHARIDIC ACID | PP1 and PP2A inhibitor. |
| −1.03 | 0.17 | 5-IODOTUBERCIDIN | Inhibits ERK2, adenosine kinase,CK1, CK2, and insulin receptor kinase. |
| 0.38 | 0.04 | Arachidonoyl alanine | Endocannabinoid |
| 0.43 | 0.07 | QUININE | POTASSIUM CHANNELS |
| 0.44 | 0.17 | AM 92016 | POTASSIUM CHANNELS |
| 0.44 | 0.16 | U-0126 | MEK inhibitor. |
| 0.46 | 0.02 | SB-202190 | p38 MAP kinase inhibitor. |
| 0.48 | 0.22 | TYRPHOSTIN 47 | EGF receptor kinase inhibitor. |
| 0.49 | 0.13 | Dihomo-gamma-linolenoyl glycine | Endocannabinoid |
| 0.52 | 0.19 | ML-9 | MLC kinase inhibitor. |
| 0.56 | 0.21 | PENITREM A | POTASSIUM CHANNELS |
| 0.61 | 0.37 | PALMITOYL-DL-CARNITINE CI | PKC inhibitor. |
| 0.61 | 0.21 | H-9 | Protein kinase inhibitor. |
| 0.63 | 0.07 | AMIODARONE | CALCIUM CHANNELS |
| 0.64 | 0.16 | NIFEDIPINE | CALCIUM CHANNELS |
| 0.68 | 0.44 | NICARDIPINE | CALCIUM CHANNELS |
| 0.69 | 0.07 | PIMOZIDE | CALCIUM CHANNELS |
| 0.72 | 0.41 | LOPERAMIDE | CALCIUM CHANNELS |
| 0.72 | 0.32 | ML-7 | MLC kinase inhibitor. |
| 0.74 | 0.47 | BEPRIDIL | CALCIUM CHANNELS |
| 0.75 | 0.33 | KN-93 | CaM kinase II inhibitor. |
| 0.85 | 0.21 | LY 294002 | Phosphatidylinositol 3-kinase inhibitor. |
| 1.14 | 0.63 | HYPERICIN | Protein kinase C inhibitor. |
| 1.27 | 0.07 | ROTTLERIN | PKC delta inhibitor. |
| 1.37 | 0.26 | WORTMANNIN | Phosphatidylinositol 3-kinase inhibitor. |
| 1.59 | 0.91 | AG-879 | Tyrosine kinase inhibitor. |
| 1.69 | 0.8 | TYRPHOSTIN 9 | PDGF receptor tyrosine kinase inhibitor. |
| 1.75 | 0.26 | DICHLOROBENZAMIL | CALCIUM CHANNELS |
| −0.21 | 0.44 | DMSO | Control |

Dose Response Curves and RT-PCR Verification

Figure 8:
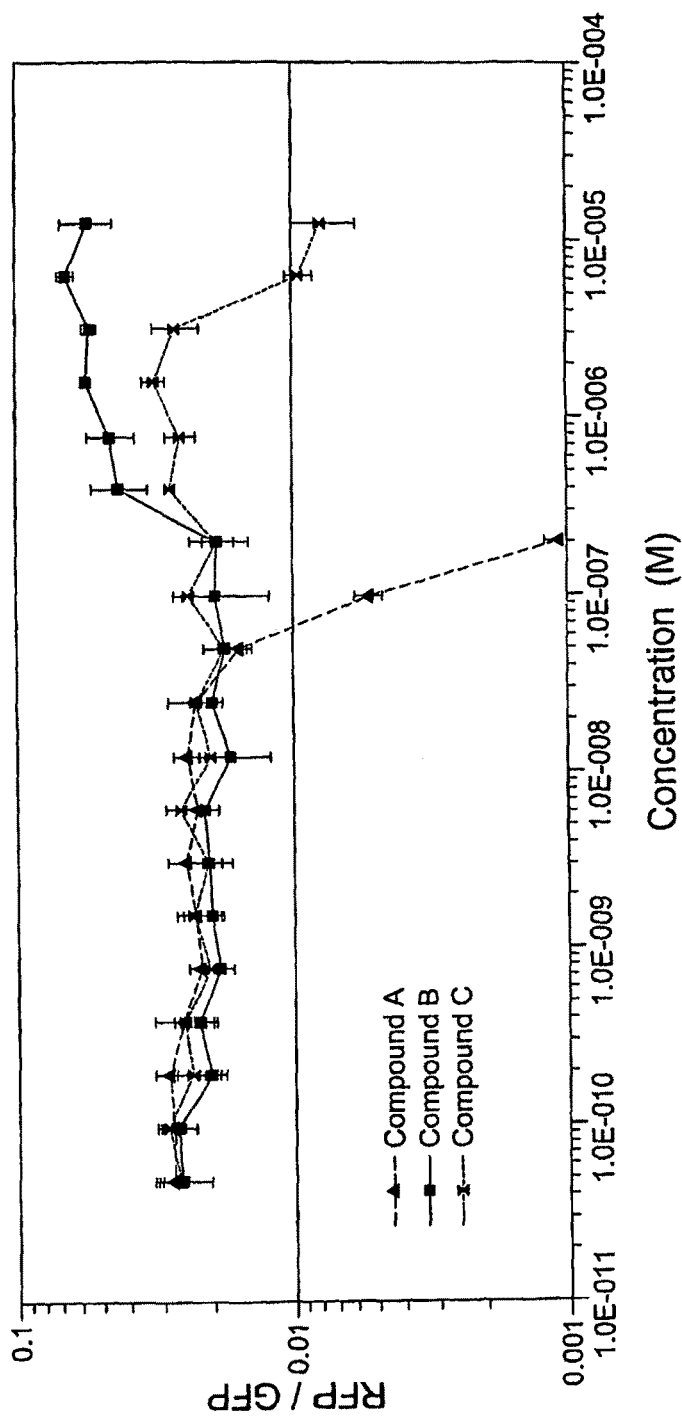
FIG. 8 shows the effect of increasing doses of three compounds identified from the high-throughput screens on the RFP/GFP ratio.
Figure 9:
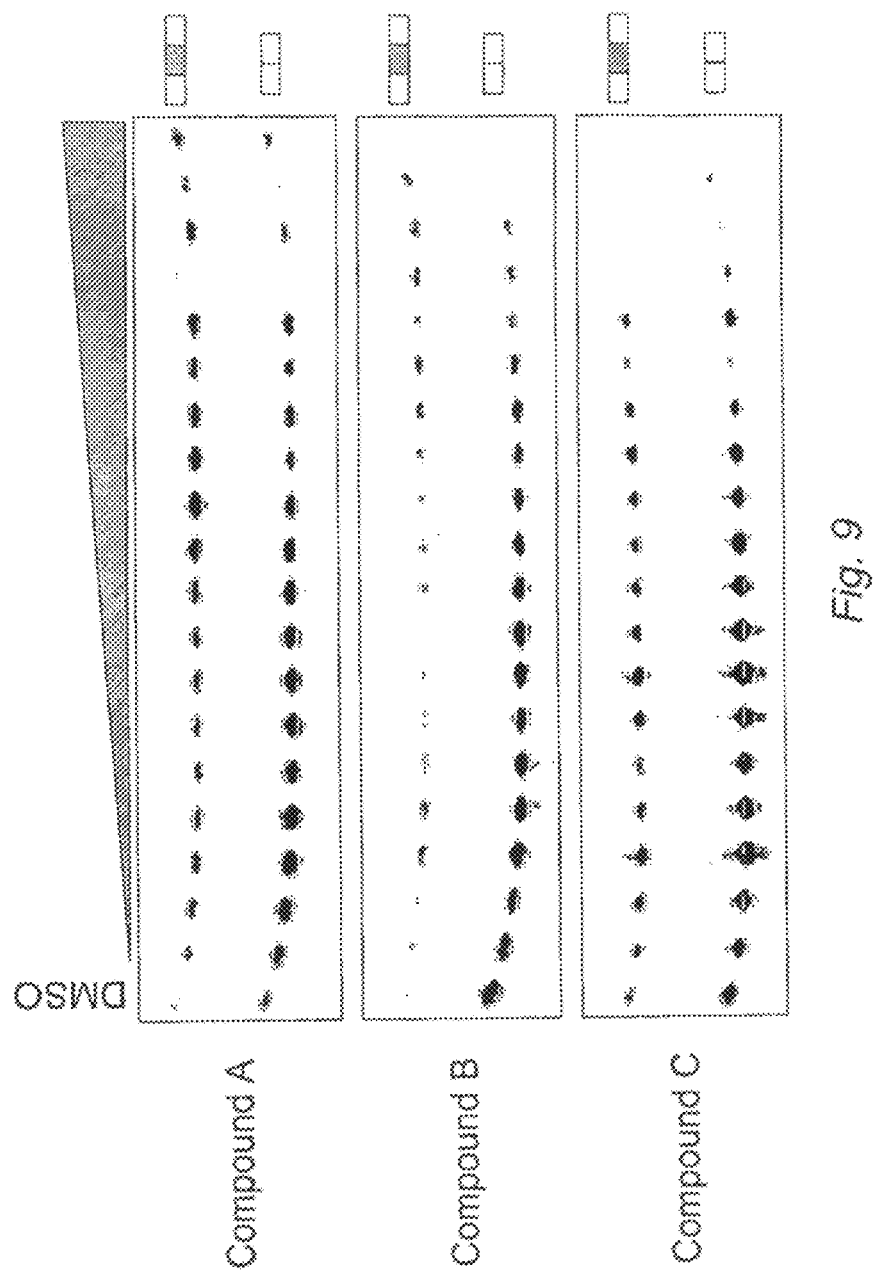
FIG. 9 shows the effect of increasing doses of three compounds identified from the high-throughput screens on the splicing of the reporter pre-mRNA as determined by RT-PCR.

Compounds identified from the screen were added in increasing concentrations to cells carrying the reporter construct to verify their effect on alternative pre-mRNA splicing. The splicing of the reporter was monitored both by fluorimetry and RT-PCR. FIG. 8 shows the change in the RFP to GFP ratio as three compounds were titrated to cells carrying the reporter. FIG. 9 shows the results of the RT-PCR amplification of the reporter mRNA. The ratio of the RFP to GFP fluorescence correctly determined the splicing pattern change induced by Compounds B and C. However, the fluorimetric data predicted increased exon skipping in the nanomolar range for Compound C, while the RT-PCR assay demonstrated increased exon inclusion.

Figure 10:
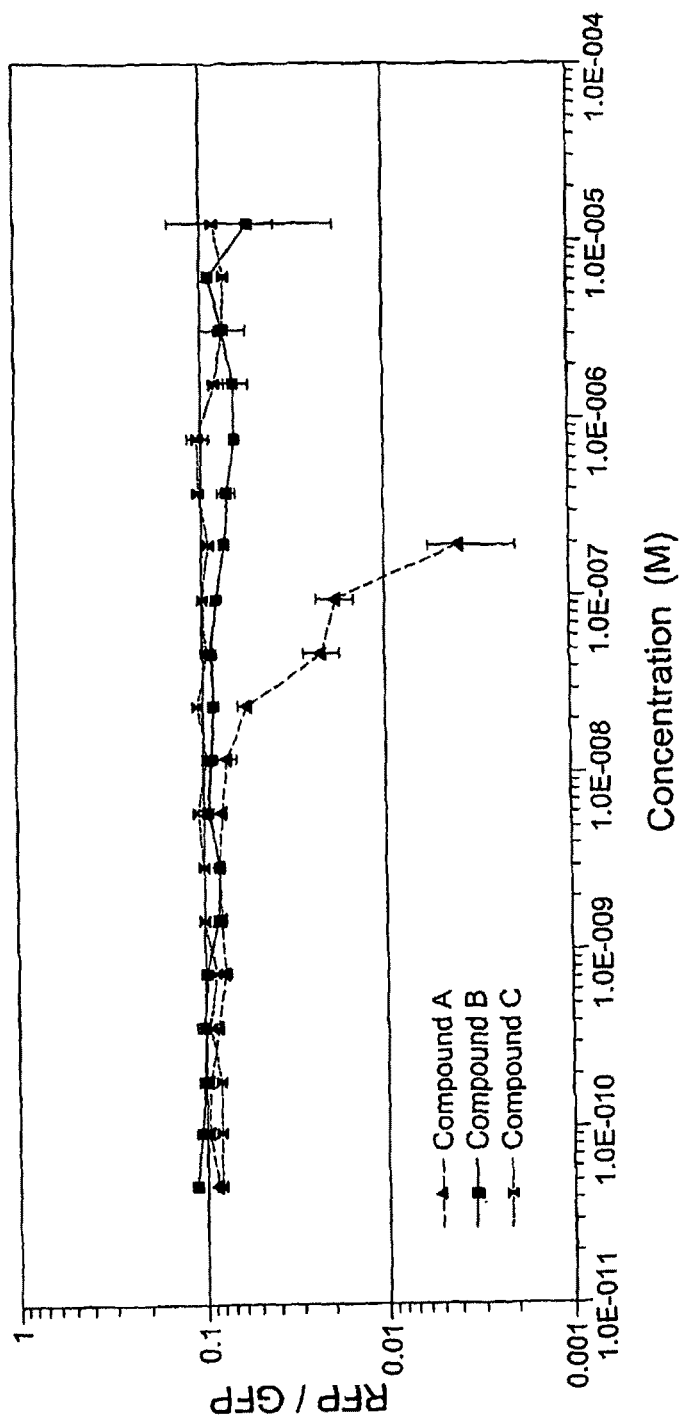
FIG. 10 shows the effect of increasing doses of three compounds identified from the high-throughput screens on the RFP/GFP ratio as determined using two single intron reporter constructs.

One possible explanation is that Compound C inhibits the scanning of the mRNA by the ribosome. Consequently, the translation of the downstream RFP open reading frame is inhibited while GFP expression is unaffected. To control for this effect, two single intron reporter constructs were used that produce the same two mRNAs as the splicing reporter construct, but are not spliced alternatively (see, FIGS. 2A-B). As shown in FIG. 10, Compound C rapidly lowered the RFP to GFP ratio in cells transfected with the two single intron reporters. This indicates that in addition to its effect on alternative splicing, Compound C inhibits translation using ATG codons located far downstream from the beginning of the mRNA sequence.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

TABLE OF SEQUENCES

SEQ ID NO: 1:
Kozak consensus sequence
(GCC)GCC(A/G)CCAUGG

SEQ ID NO: 2:
Intron sequence of reporter construct
GTAAGTATCAAGGTTACAAGACAGGTTTAAGGAGACCAATAGAAACTGGG
CATGTGGAGACAGAGAAGACTCTTGGGTTTCTGAATTCATTGGATCCACC
ATGGTGGCTTAGATCCGGACATGTGGAGACAGAGAAGACTCTTGAATTTA
TGATTGACACTGACTCTATCTGCCTATTGGTCTATTTTCCCTCCCTCAG SEQ ID NO: 3:
First exon sequence of reporter construct ending in A
AGATCTACCATTGGTGCACCTGACTCCTGAGGAGAAGTCTGCCGTTACTG
CCCTGTGGGGCAAGGTGAACGTGGAAGAGTTGGTGGTGAGGCCCTGGGCC
ACCA SEQ ID NO: 4:
Modified EGFP sequence
TGGTGAGCAAGGGCGAGGAGCTGTTCACCGGGGTGGTGCCCATCCTGGTC
GAGCTGGACGGCGACGTAAACGGCCACAAGTTCAGCGTGTCCGGCGAGGG
CGAGGGCGACGCCACCTACGGCAAGCTGACCCTGAAGTTCATCTGCACCA
CCGGCAAGCTGCCCGTGCCCTGGCCCACCCTCGTGACCACCCTGACCTAC
GGCGTGCAGTGCTTTAGCCGCTACCCCGACCACCTGAAGCAGCACGACTT
CTTCAAGAGTGCAATGCCCGAAGGCTACGTCCAGGAGCGCACCATCTTCT
TCAAGGACGACGGCAACTACAAGACCCGCGCCGAGGTGAAGTTCGAGGGC
GACACCCTGGTGAACCGCATCGAGCTGAAGGGCATCGACTTCAAGGAGGA
CGGCAACATCCTGGGGCACAAGCTGGAGTACAACTACAACAGCCACAACG
TCTATATCACCGCCGACAAGCAGAAGAACGGCATCAAGGTGAACTTCAAG
ATCCGCCACAACATCGAGGACGGCAGCGTGCAGCTCGCCGACCACTACCA
GCAGAACACCCCCATCGGCGACGGCCCCGTGCTGCTGCCCGACAACCACT
ACCTGAGCACCCAGTCCGCCCTGAGCAAAGACCCCAACGAGAAGCGCGAT
CATATGGTCCTGCTGGAGTTCGTGACCGCCGCCGGGATCACTCTCGGCAC
CGACGAGCTGTACAAGTAA SEQ ID NO: 5:
Modified mouse ornithine decarboxylase (MODC) PEST sequence

TABLE OF SEQUENCES

AAGCTTAGCCACGGCTTCCCGCCGGCGGTGGCGGCGCAGGACGACGGCAC
GCTGCCAGTGTCTTGTGCCCAGGAGAGTGGGATCGATAGACATCCAGCCG
CCTGCGCCTCCGCCAGAATTAACGTCTAA

SEQ ID NO: 6:
Destabilized DsRed-Express sequence
ATGGCCTCCTCCGAGGACGTCATCAAGGAGTTCATGCGCTTCAAGGTGCG
CATGGAGGGCTCCGTGAACGGCCACGAGTTCGAGATCGAGGGCGAGGGCG
AGGGCCGCCCCTACGAGGGCACCCAGACCGCCAAGCTGAAGGTGACCAAG
GGCGGCCCCCTGCCCTTCGCCTGGGACATCCTGTCCCCCCAGTTCCAGTA
CGGCTCCAAGGTGTACGTGAAGCACCCCGCCGACATCCCCGACTACAAGA
AGCTGTCCTTCCCCGAGGGCTTCAAGTGGGAGCGCGTGATGAACTTCGAG
GACGGCGGCGTGGTGACCGTGACCCAGGACTCCTCCCTGCAGGACGGCTC
CTTCATCTACAAGGTGAAGTTCATCGGCGTGAACTTCCCCTCCGACGGCC
CCGTAATGCAGAAGAAGACTATGGCGTGGGAGGCCTCCACCGAGCGCCTG
TACCCCCGCGACGGCGTGCTGAAGGGCGAGATCCACAAGGCCCTGAAGCT
GAAGGACGGCGGCCACTACCTGGTGGAGTTCAAGTCCATCTACATGGCCA
AGAAGCCCGTGCAGCTGCCCGGCTACTACTACGTGGACTCCAAGCTGGAC
ATCACCTCCCACAACGAGGACTACACCATCGTGGAGCAGTACGAGCGCGC
CGAGGGCCGCCACCACCTGTTCCTGACTAGTGATATCAGCCATGGCTTCC
CGCCGGCGGTGGCGGCGCAGGATGATGGCACGCTGCCCATGTCTTGTGCC
CAGGAGAGCGGGATGGACCGTCACCCTGCAGCCTGTGCTTCTGCTAGGAT
CAATGTGTAG SEQ ID NO: 7:
Modified EYFP sequence
TGGTGAGCAAAGGCGAGGAGCTGTTCACCGGCGTGGTGCCCATCCTGGTC
GAGCTGGACGGCGACGTAAACGGCCACAAGTTCAGCGTGTCCGGCGAGGG
CGAGGGCGACGCCACCTACGGCAAGCTGACCCTGAAGTTCATCTGCACCA CCGGCAAGCTGCCCGTGCCCTGGCCCACCCTCGTGACCACCTTCGGCTAC
GGCCTGCAGTGCTTCGCCCGCTACCCCGACCACCTGAAGCAGCACGACTT
CTTCAAGAGTGCAATGCCCGAAGGCTACGTCCAGGAGCGCACCATCTTCT
TCAAGGACGACGGCAACTACAAGACCCGCGCCGAGGTGAAGTTCGAGGGC
GACACCCTGGTGAACCGCATCGAGCTGAAGGGCATCGACTTCAAGGAGGA
CGGCAACATCCTGGGGCACAAGCTGGAGTACAACTACAACAGCCACAACG
TCTATATCACCGCCGACAAGCAGAAGAACGGCATCAAGGTGAACTTCAAG
ATCCGCCACAACATCGAGGACGGCAGCGTGCAGCTCGCCGACCACTACCA
GCAGAACACCCCCATCGGCGACGGCCCCGTGCTGCTGCCCGACAACCACT
ACCTGAGCTACCAGTCCGCCCTGAGCAAAGACCCCAACGAGAAGCGCGAT
CATATGGTCCTGCTGGAGTTCGTGACCGCCGCCGGGATCACTCTCGGCAC
CGACGAGCTCTACAAGTAA SEQ ID NO: 8:
First exon sequence of reporter construct ending
in G
AGATCTACCATTGGTGCACCTGACTCCTGAGGAGAAGTCTGCCGTTACTG
CCCTGTGGGGCAAGGTGAACGTGGAAGAGTTGGTGGTGAGGCCCTGGGCC
ACCAG SEQ ID NO: 9:
Homo sapiens microtubule-associated protein tau
gene, exon 10 sequence
CGAGCAAGCAGCGGGTCCAGGGTGGCGTGTCACTCATCCTTTTTTCTGGC
TACCAAAGGTGCAGATAATTAATAAGAAGCTGGATCTTAGCAACGTCCAG
TCCAAGTGTGGCTCAAAGGATAATATCAAACACGTCCCGGGAGGCGGCAG
TGTGAGTACCTTCACACGTCCCATGCGCCGTGCTGTGGCTTGAATTATTA
GGAAGTGGTGTGAGTCGTACAC

What is claimed is:

1. An alternative pre-mRNA splicing reporter construct comprising a promoter operably linked to a nucleic acid sequence encoding first and second fluorescent proteins,
    wherein the nucleic acid sequence encoding the first fluorescent protein comprises a first start codon that resides in a Kozak consensus sequence and that is interrupted by a cassette comprising a nucleic acid with alternative splice sites, wherein the alternative splice sites produce at least two alternative splice products,
    wherein the nucleic acid sequence encoding the second fluorescent protein comprises a second start codon that resides in a Kozak consensus sequence,
    wherein the nucleic acid sequence encoding the second fluorescent protein is 3' to the nucleic acid sequence encoding the first fluorescent protein,
    wherein the first start codon is the only start codon in a Kozak consensus sequence that resides upstream of the second start codon.

2. The reporter construct of claim 1, wherein the nucleic acid with alternative splice sites is selected from the group consisting of an exon flanked by two introns, an intron with two 5' splice sites and one 3' splice site, and an intron with one 5' splice site and two 3' splice sites.

3. The reporter construct of claim 1, wherein the promoter comprises a human cytomegalovirus (CMV) promoter.

4. The reporter construct of claim 1, wherein the first and second fluorescent proteins are independently selected from the group consisting of a green fluorescent protein, red fluorescent protein, yellow fluorescent protein, cyan fluorescent protein, blue fluorescent protein, and variants thereof.

5. The reporter construct of claim 4, wherein the green fluorescent protein comprises an enhanced green fluorescent protein (EGFP) or a variant thereof.

6. The reporter construct of claim 4, wherein the red fluorescent protein comprises a *Discosoma striata* red fluorescent protein (DsRed) or a variant thereof.

7. The reporter construct of claim 2, wherein the exon comprises exon 10 of the human tau gene.

8. A method for monitoring alternative pre-mRNA splicing in a test cell, the method comprising:
    (a) introducing the reporter construct of claim 1 into the test cell;
    (b) transcribing a pre-mRNA sequence from the reporter construct; and
    (c) detecting alternative splicing from the pre-mRNA sequence,
    wherein expression of the first fluorescent protein indicates that a first alternative splice product has been produced, and wherein expression of the second fluorescent protein indicates that a second alternative splice product has been produced.

9. The method of claim 8, further comprising introducing a control reporter construct into a control cell to detect the presence or absence of a difference in ribosome scanning processivity between the first and the second alternative splice products,
    wherein the control cell is a cell of the same or similar tissue type as the test cell; and
    wherein the control reporter constructs comprise a reporter construct without the alternative exon and one of the introns, or
    wherein the control reporter constructs comprise a reporter construct without any introns.

10. The method of claim 9, wherein two control reporter constructs are introduced into the control cell, a first control reporter detecting the presence or absence of a difference in ribosome scanning processivity in the first alternative splice product, and a second control reporter detecting the presence or absence of a difference in ribosome scanning processivity in the second alternative splice product.

11. The method of claim 8, further comprising calculating a ratio of the expression levels of the first and second fluorescent proteins in the test cell.

12. The method of claim 11, wherein the expression ratio in the test cell is compared to an expression ratio of the first and second fluorescent proteins in the control cell.

13. The method of claim 12, wherein a change in the expression ratio in the test cell relative to the control cell indicates a modulation in alternative pre-mRNA splicing.

14. The method of claim 13, wherein the modulation in alternative pre-mRNA splicing is associated with a disease characterized by alternative splicing.

15. The method of claim 14, wherein the disease is selected from the group consisting of tumorigenesis and cell transformation, neurodegenerative disorders, metabolic diseases and disorders, angiogenesis, muscular dystrophies, and inflammatory and autoimmune responses.

16. A method for identifying a compound that modulates alternative pre-mRNA splicing, the method comprising:
   (a) contacting a test cell expressing the reporter construct of claim 1 with a compound; and
   (b) determining the effect of the compound on the expression of the first and second fluorescent proteins, thereby identifying a compound that modulates alternative pre-mRNA splicing.

17. The method of claim 16, further comprising calculating a ratio of the expression levels of the first and second fluorescent proteins in the test cell.

18. A kit comprising the reporter construct of claim 1 and directions for introducing the reporter construct into a cell.

19. The kit of claim 18, further comprising directions for detecting the expression of the first and second fluorescent proteins.

* * * * *

SEQUENCE LISTING

<160> NUMBER OF SEQ ID NOS: 10

<210> SEQ ID NO 1
<211> LENGTH: 13
<212> TYPE: RNA
<213> ORGANISM: Artificial Sequence
<220> FEATURE:
<223> OTHER INFORMATION: Kozak eukaryotic mRNA consensus sequence

<400> SEQUENCE: 1
gccgccrcca ugg                                                         13

<210> SEQ ID NO 2
<211> LENGTH: 199
<212> TYPE: DNA
<213> ORGANISM: Artificial Sequence
<220> FEATURE:
<223> OTHER INFORMATION: intron sequence of reporter construct, human
      beta-globin gene intron, reporter intron carrying EcoRI and BamHI
      restriction sites

<400> SEQUENCE: 2
gtaagtatca aggttacaag acaggtttaa ggagaccaat agaaactggg catgtggaga      60
cagagaagac tcttgggttt ctgaattcat tggatccacc atggtggctt agatccggac     120
atgtggagac agagaagact cttgaattta tgattgacac tgactctatc tgcctattgg    180
tctattttcc ctccctcag                                                  199

<210> SEQ ID NO 3
<211> LENGTH: 104
<212> TYPE: DNA
<213> ORGANISM: Artificial Sequence
<220> FEATURE:
<223> OTHER INFORMATION: first exon sequence of reporter construct
      ending in A nucleotide of start codon of first reporter protein

<400> SEQUENCE: 3

```
agatctacca ttggtgcacc tgactcctga ggagaagtct gccgttactg ccctgtgggg    60
caaggtgaac gtggaagagt tggtggtgag gccctgggcc acca                    104
```

<210> SEQ ID NO 4
<211> LENGTH: 719
<212> TYPE: DNA
<213> ORGANISM: Artificial Sequence
<220> FEATURE:
<223> OTHER INFORMATION: modified enhanced Aequorea victoria Pacific
      Northwest jellyfish green fluorescent proten (EGFP) sequence,
      destabilized EGFP variant with modified internal ATG condons or
      Kazak consensus sequences, first reporter protein

<400> SEQUENCE: 4

```
tggtgagcaa gggcgaggag ctgttcaccg gggtggtgcc catcctggtc gagctggacg    60
gcgacgtaaa cggccacaag ttcagcgtgt ccggcgaggg cgagggcgac gccacctacg   120
gcaagctgac cctgaagttc atctgcacca ccggcaagct gcccgtgccc tggcccaccc   180
tcgtgaccac cctgacctac ggcgtgcagt gctttagccg ctaccccgac cacctgaagc   240
agcacgactt cttcaagagt gcaatgcccg aaggctacgt ccaggagcgc accatcttct   300
tcaaggacga cggcaactac aagacccgcg ccgaggtgaa gttcgagggc gacacccctgg  360 tgaaccgcat cgagctgaag ggcatcgact tcaaggagga cggcaacatc ctggggcaca   420
agctggagta caactacaac agccacaacg tctatatcac cgccgacaag cagaagaacg   480
gcatcaaggt gaacttcaag atccgccaca acatcgagga cggcagcgtg cagctcgccg   540
accactacca gcagaacacc cccatcggcg acggccccgt gctgctgccc gacaaccact   600
acctgagcac ccagtccgcc ctgagcaaag accccaacga gaagcgcgat catatggtcc   660
tgctggagtt cgtgaccgcc gccgggatca ctctcggcac cgacgagctg tacaagtaa    719
```

<210> SEQ ID NO 5
<211> LENGTH: 129
<212> TYPE: DNA
<213> ORGANISM: Artificial Sequence
<220> FEATURE:
<223> OTHER INFORMATION: modified mouse ornithine decarboxylase (MODC)
      PEST sequence with mutations to internal ATG codons and to
      decrease wild-type sequence homology

<400> SEQUENCE: 5

```
aagcttagcc acggcttccc gccggcggtg gcggcgcagg acgacggcac gctgccagtg    60
tcttgtgccc aggagagtgg gatcgataga catccagccg cctgcgcctc cgccagaatt   120
aacgtctaa                                                           129
```

<210> SEQ ID NO 6
<211> LENGTH: 810
<212> TYPE: DNA
<213> ORGANISM: Artificial Sequence
<220> FEATURE:
<223> OTHER INFORMATION: destabilized Discosoma striata coral red
      fluorescent protein (RFP) DsRed-Express sequence, second reporter
      protein

<400> SEQUENCE: 6

```
atggcctcct ccgaggacgt catcaaggag ttcatgcgct tcaaggtgcg catggagggc    60
tccgtgaacg gccacgagtt cgagatcgag ggcgagggcg agggccgccc ctacgagggc   120
acccagaccg ccaagctgaa ggtgaccaag ggcggccccc tgcccttcgc ctgggacatc   180
```

```
ctgtcccccc agttccagta cggctccaag gtgtacgtga agcaccccgc cgacatcccc    240
gactacaaga agctgtcctt ccccgagggc ttcaagtggg agcgcgtgat gaacttcgag    300
gacggcggcg tggtgaccgt gacccaggac tcctccctgc aggacggctc cttcatctac    360
aaggtgaagt tcatcggcgt gaacttcccc tccgacggcc ccgtaatgca gaagaagact    420
atgggctggg aggcctccac cgagcgcctg taccccgcg acggcgtgct gaagggcgag     480
atccacaagg ccctgaagct gaaggacggc ggccactacc tggtggagtt caagtccatc    540
tacatggcca agaagcccgt gcagctgccc ggctactact acgtggactc caagctggac    600
atcacctccc acaacgagga ctacaccatc gtggagcagt acgagcgcgc cgagggccgc    660
caccacctgt tcctgactag tgatatcagc catggcttcc cgccggcggt ggcggcgcag    720
gatgatggca cgctgcccat gtcttgtgcc caggagagcg ggatggaccg tcaccctgca    780
gcctgtgctt ctgctaggat caatgtgtag                                     810

<210> SEQ ID NO 7
<211> LENGTH: 719
<212> TYPE: DNA
<213> ORGANISM: Artificial Sequence
<220> FEATURE:
<223> OTHER INFORMATION: modified enhanced yellow fluorescent protein
      (EYFP) sequence

<400> SEQUENCE: 7
tggtgagcaa aggcgaggag ctgttcaccg gcgtggtgcc catcctggtc gagctggacg    60
gcgacgtaaa cggccacaag ttcagcgtgt ccggcgaggg cgagggcgac gccacctacg    120
gcaagctgac cctgaagttc atctgcacca ccggcaagct gcccgtgccc tggcccaccc    180
tcgtgaccac cttcggctac ggcctgcagt gcttcgcccg ctaccccgac cacctgaagc    240
agcacgactt cttcaagagt gcaatgcccg aaggctacgt ccaggagcgc accatcttct    300
tcaaggacga cggcaactac aagacccgcg ccgaggtgaa gttcgagggc gacaccctgg    360
tgaaccgcat cgagctgaag ggcatcgact tcaaggagga cggcaacatc ctggggcaca    420
agctggagta caactacaac agccacaacg tctatatcac cgccgacaag cagaagaacg    480
gcatcaaggt gaacttcaag atccgccaca acatcgagga cggcagcgtg cagctcgccg    540
accactacca gcagaacacc cccatcggcg acggccccgt gctgctgccc gacaaccact    600
acctgagcta ccagtccgcc ctgagcaaag accccaacga aagcgcgat catatggtcc    660 tgctggagtt cgtgaccgcc gccgggatca ctctcggcac cgacgagctc tacaagtaa    719

<210> SEQ ID NO 8
<211> LENGTH: 105
<212> TYPE: DNA
<213> ORGANISM: Artificial Sequence
<220> FEATURE:
<223> OTHER INFORMATION: first exon sequence of reporter construct
      ending in G

<400> SEQUENCE: 8
agatctacca ttggtgcacc tgactcctga ggagaagtct gccgttactg ccctgtgggg    60
caaggtgaac gtggaagagt tggtggtgag gccctgggcc accag                    105

<210> SEQ ID NO 9
<211> LENGTH: 222
<212> TYPE: DNA
<213> ORGANISM: Homo sapiens
<220> FEATURE:
<221> NAME/KEY: exon
<222> LOCATION: (59)..(151)
```

-continued

```
<223> OTHER INFORMATION: microtubule-associated protein tau (MAPT) gene,
      exon 10 sequence containing short flanking intronic sequences from
      introns 9 and 10

<400> SEQUENCE: 9
cgagcaagca gcgggtccag ggtggcgtgt cactcatcct tttttctggc taccaaag           58 gtg cag ata att aat aag aag ctg gat ctt agc aac gtc cag tcc aag          106
Val Gln Ile Ile Asn Lys Lys Leu Asp Leu Ser Asn Val Gln Ser Lys
1               5                   10                  15 tgt ggc tca aag gat aat atc aaa cac gtc ccg gga ggc ggc agt              151
Cys Gly Ser Lys Asp Asn Ile Lys His Val Pro Gly Gly Gly Ser
                20                  25                  30 gtgagtacct tcacacgtcc catgcgccgt gctgtggctt gaattattag gaagtggtgt        211
gagtcgtaca c                                                             222

<210> SEQ ID NO 10
<211> LENGTH: 12
<212> TYPE: DNA
<213> ORGANISM: Artificial Sequence
<220> FEATURE:
<223> OTHER INFORMATION: portion of sequence of two-color, pFlare5A
      Tau10b, control single intron, pFlare2A and pFlare5G fluorescent
      reporter constructs

<400> SEQUENCE: 10
taggccacca tg                                                             12
```